US012042515B2

United States Patent
Qian et al.

(10) Patent No.: US 12,042,515 B2
(45) Date of Patent: Jul. 23, 2024

(54) KILLER CELL CAPABLE OF EFFICIENTLY AND STABLY EXPRESSING ANTIBODY, AND USES THEREOF

(71) Applicants: Shanghai Cell Therapy Research Institute, Shanghai (CN); Shanghai Cell Therapy Group Co., Ltd., Shanghai (CN)

(72) Inventors: Qijun Qian, Shanghai (CN); Huajun Jin, Shanghai (CN); Jieying Xu, Shanghai (CN); Linfang Li, Shanghai (CN); Zhenlong Ye, Shanghai (CN); Zhou He, Shanghai (CN); Lianzhen Cui, Shanghai (CN); Hongping Wu, Shanghai (CN)

(73) Assignees: Shanghai Cell Therapy Research Institute, Shanghai (CN); Shanghai Cell Therapy Group Co., Ltd., Shanghai (CN)

( * ) Notice: Subject to any disclaimer, the term of this patent is extended or adjusted under 35 U.S.C. 154(b) by 1274 days.

(21) Appl. No.: 16/311,084

(22) PCT Filed: Jun. 19, 2017

(86) PCT No.: PCT/CN2017/088955
§ 371 (c)(1),
(2) Date: Mar. 30, 2020

(87) PCT Pub. No.: WO2017/219934
PCT Pub. Date: Dec. 28, 2017

(65) Prior Publication Data
US 2020/0289561 A1    Sep. 17, 2020

(30) Foreign Application Priority Data
Jun. 20, 2016 (CN) .......................... 201610443886.6

(51) Int. Cl.
*A61K 35/17* (2015.01)
*A61P 35/00* (2006.01)
(Continued)

(52) U.S. Cl.
CPC .............. *A61K 35/17* (2013.01); *A61P 35/00* (2018.01); *C07K 16/08* (2013.01);
(Continued)

(58) Field of Classification Search
None
See application file for complete search history.

(56) References Cited

U.S. PATENT DOCUMENTS 9,399,671 B2 * 7/2016 Ellis ........................ C07K 16/00

FOREIGN PATENT DOCUMENTS

| CN | 102220283 A | 10/2011 |
| CN | 104745581 A | 7/2015 |

(Continued)

OTHER PUBLICATIONS

Chakraborty et al., Scientific Reports, 4 (7403): 1-9, Dec. 10, 2014 (Year: 2014).*
(Continued)

*Primary Examiner* — Karl J Puttlitz
(74) *Attorney, Agent, or Firm* — Banner & Witcoff, Ltd.

(57) ABSTRACT

Provided is a transgenic killer cell, the genome of which is stably integrated with a coding sequence comprising an antibody of a human Fc section, or an expression cassette of a coding sequence comprising a chimeric antigen receptor or an inhibitory or agonistic antibody, and an inverted terminal repeat sequence from a transposon at both ends. Also provided is a pharmaceutical composition comprising the transgenic killer cell, and uses thereof.

14 Claims, 14 Drawing Sheets

Specification includes a Sequence Listing.

(51) Int. Cl.
  *C07K 16/08* (2006.01)
  *C07K 16/28* (2006.01)
  *C07K 16/30* (2006.01)
  *C12N 5/0783* (2010.01)
  *C12N 5/10* (2006.01)
  *C12N 15/82* (2006.01)

(52) U.S. Cl.
  CPC .......... *C07K 16/2818* (2013.01); *C07K 16/30* (2013.01); *C12N 5/0646* (2013.01); *C12N 5/10* (2013.01); *C12N 15/8206* (2013.01); *C07K 2317/24* (2013.01); *C07K 2317/52* (2013.01); *C07K 2317/622* (2013.01); *C07K 2317/76* (2013.01); *C07K 2319/03* (2013.01); *C07K 2319/33* (2013.01); *C12N 2310/12* (2013.01); *C12N 2510/00* (2013.01); *C12N 2800/90* (2013.01)

(56) References Cited

FOREIGN PATENT DOCUMENTS

| CN | 105154473 A | 12/2015 |
| CN | 105330750 A | 2/2016 |
| CN | 105331585 A | 2/2016 |
| CN | 105331586 A | 2/2016 |
| WO | 2012079000 | * 6/2012 |
| WO | 2014134165 A1 | 9/2014 |
| WO | 2016203048 | * 12/2016 |

OTHER PUBLICATIONS

Yusa et al., Nat Methods. May 2009; 6(5): 363-369 (Year: 2009).*
Keith et al., BMC Molecular Biology; 2008, 9U2: 1-13 (Year: 2008).*
Urasaki et al., Genetics 174 (2), 639-649, 2006 (Year: 2006).*
Zhang, Xinwei et al., "Clinical Research Status of PD-1 Blocking Antibody in the Treatment of Tumor", Medicine and Philosophy, vol. 36, No. 2B, Feb. 28, 2015, ISSN: 1002-0772.
International Search Report and Written Opinion dated Sep. 27, 2017, for corresponding International Application No. PCT/CN2017/088955; International Filing Date: Jun. 19, 2017 consisting of 8-pages.
Chinese Office Action dated Mar. 31, 2021, for corresponding Chinese Office Action 201610443886.6; consisting of 10-pages.

* cited by examiner

SEQUENCE LISTING

```
<160> NUMBER OF SEQ ID NOS: 14

<210> SEQ ID NO 1
<211> LENGTH: 21
<212> TYPE: DNA
<213> ORGANISM: artificial sequence
<220> FEATURE:
<223> OTHER INFORMATION: primer

<400> SEQUENCE: 1
cgataggacg ctgatcttaa t                                              21
```

<210> SEQ ID NO 2
<211> LENGTH: 16
<212> TYPE: DNA
<213> ORGANISM: artificial sequence
<220> FEATURE:
<223> OTHER INFORMATION: primer

<400> SEQUENCE: 2
tacctgcgac tagaat                                                     16

<210> SEQ ID NO 3
<211> LENGTH: 2190
<212> TYPE: DNA
<213> ORGANISM: artificial sequence
<220> FEATURE:
<223> OTHER INFORMATION: antiPD1 coding sequence

<400> SEQUENCE: 3
gaattcgcca ccatggaagc cccagctcag cttctcttcc tcctgctact ctggctccca      60
gataccaccg gacaggtgta cttggtagag tctgggggag gcgtggtcca gcctggggagg    120 tccctgagac tctcctgtgc agcgtctgga ttcaccttca gtaactatgg catgcactgg    180
gtccgccagg ctccaggcaa ggggctggag tgggtggcac ttatatggta tgatggaagt    240
aataaatact atgcagactc cgtgaagggc cgattcacca tctccagaga caattccaag    300
aacacgctgt atctgcaaat gaccagtctg agagtcgagg acacggctgt gtattattgt    360
gcgagcaacg ttgaccattg gggccaggga accctggtca ccgtctcctc agcttccacc    420
aagggcccat ccgtcttccc cctggcgccc tgctccagga gcacctccga gagcacagcc    480
gccctgggct gcctggtcaa ggactacttc cccgaaccgg tgacggtgtc gtggaactca    540
ggcgccctga ccagcggcgt gcacaccttc ccggctgtcc tacagtcctc aggactctac    600
tccctcagca gcgtggtgac cgtgccctcc agcagcttgg gcacgaagac ctacacctgc    660
aacgtagatc acaagcccag caacaccaag gtggacaaga gagttgagtc caaatatggt    720
cccccatgcc caccatgccc agcacctgag ttcctggggg gaccatcagt cttcctgttc    780
cccccaaaac ccaaggacac tctcatgatc tcccggaccc ctgaggtcac gtgcgtggtg    840
gtggacgtga gccaggaaga ccccgaggtc cagttcaact ggtacgtgga tggcgtggag    900
gtgcataatg ccaagacaaa gccgcgggag gagcagttca acagcacgta ccgtgtggtc    960
agcgtcctca ccgtcctgca ccaggactgg ctgaacggca aggagtacaa gtgcaaggtc   1020
tccaacaaag gctcccgtc ctccatcgag aaaaccatct ccaaagccaa agggcagccc    1080
cgagagccac aggtgtacac cctgccccca tcccaggagg agatgaccaa gaaccaggtc   1140
agcctgacct gcctggtcaa aggcttctac cccagcgaca tcgccgtgga gtgggagagc   1200
aatgggcagc cggagaacaa ctacaagacc acgcctcccg tgctggactc cgacggctcc   1260
ttcttcctct acagcaggct aaccgtggac aagagcaggt ggcaggaggg gaatgtcttc   1320
tcatgctccg tgatgcatga ggctctgcac aaccactaca cacagaagag cctctccctg   1380
tctctgggta aacgtaaaag gcgagctcct gttaaacaga ctttgaattt tgaccttctc    1440
aagttggcgg gagacgtcga gtccaaccct gggcccatgg aagccccagc tcagcttctc   1500
ttcctcctgc tactctggct cccagatacc accggagaaa ttgtgttgac acagtctcca   1560
gccaccctgt ctttgtctcc aggggaaaga gccaccctct cctgcagggc cagtcagagt   1620
gttagtagtt acttagcctg gtaccaacag aaacctggcc aggctcccag gctcctcatc   1680
tatgatgcat ccaacagggc cactggcatc ccagccaggt tcagtggcag tgggtctggg   1740

| | |
|---|---|
| acagacttca ctctcaccat cagcagccta gagcctgaag attttgcagt ttattactgt | 1800 |
| cagcagagta gcaactggcc tcggacgttc ggccaaggga ccaaggtgga aatcaaacga | 1860 |
| actgtggctg caccatctgt cttcatcttc ccgccatctg atgagcagtt gaaatctgga | 1920 |
| actgcctctg ttgtgtgcct gctgaataac ttctatccca gagaggccaa agtacagtgg | 1980 |
| aaggtggata acgccctcca atcgggtaac tcccaggaga gtgtcacaga gcaggacagc | 2040 |
| aaggacagca cctacagcct cagcagcacc ctgacgctga gcaaagcaga ctacgagaaa | 2100 |
| cacaaagtct acgcctgcga agtcacccat cagggcctga gctcgcccgt cacaaagagc | 2160 |
| ttcaacaggg gagagtgttg ataagtcgac | 2190 |

<210> SEQ ID NO 4
<211> LENGTH: 1071
<212> TYPE: DNA
<213> ORGANISM: artificial sequence
<220> FEATURE:
<223> OTHER INFORMATION: CD20BR coding sequence

<400> SEQUENCE: 4

| | |
|---|---|
| gaattcgcca ccatggagtt ttggctgagc tgggttttcc ttgttgctat tttaaaaggt | 60 |
| gtccagtgta acatatacaa ctgtgaacca gctaatccct ctgagaaaaa ctccccatct | 120 |
| acccaatact gttacagcat acaatctctg ggtggaggtg gaggtggagg tggaggtatc | 180 |
| tacatctggg cgcccttggc cgggacttgt ggggtccttc tcctgtcact ggttatcacc | 240 |
| ctttactgca accacaggaa ccgtaaaagg cgagctcctg ttaaacagac tttgaatttt | 300 |
| gaccttctca agttggcggg agacgtcgag tccaaccctg ggcccatggt gagcaagcag | 360 |
| atcctgaaga acaccggcct gcaggagatc atgagcttca aggtgaacct ggagggcgtg | 420 |
| gtgaacaacc acgtgttcac catggagggc tgcggcaagg gcaacatcct gttcggcaac | 480 |
| cagctggtgc agatccgcgt gaccaagggc gcccccctgc ccttcgcctt cgacatcctg | 540 |
| agccccgcct tccagtacgg caaccgcacc ttcaccaagt accccgagga catcagcgac | 600 |
| ttcttcatcc agagcttccc cgccggcttc gtgtacgagc gcaccctgcg ctacgaggac | 660 |
| ggcggcctgg tggagatccg cagcgacatc aacctgatcg aggagatgtt cgtgtaccgc | 720 |
| gtggagtaca agggccgcaa cttccccaac gacggccccg tgatgaagaa gaccatcacc | 780 |
| ggcctgcagc ccagcttcga ggtggtgtac atgaacgacg gcgtgctggt gggccaggtg | 840 |
| atcctggtgt accgcctgaa cagcggcaag ttctacagct gccacatgcg caccctgatg | 900 |
| aagagcaagg gcgtggtgaa ggacttcccc gagtaccact tcatccagca ccgcctggag | 960 |
| aagacctacg tggaggacgg cggcttcgtg gagcagcacg agaccgccat cgcccagctg | 1020 |
| accagcctgg gcaagcccct gggcagcctg cacgagtggg tgtgagtcga c | 1071 |

<210> SEQ ID NO 5
<211> LENGTH: 20
<212> TYPE: DNA
<213> ORGANISM: artificial sequence
<220> FEATURE:
<223> OTHER INFORMATION: primer

<400> SEQUENCE: 5

| | |
|---|---|
| atctccaaag ccaagggca | 20 |

<210> SEQ ID NO 6
<211> LENGTH: 20
<212> TYPE: DNA

```
<213> ORGANISM: artificial sequence
<220> FEATURE:
<223> OTHER INFORMATION: primer

<400> SEQUENCE: 6
cgatgtcgct ggggtagaag                                                    20

<210> SEQ ID NO 7
<211> LENGTH: 2214
<212> TYPE: DNA
<213> ORGANISM: artificial sequence
<220> FEATURE:
<223> OTHER INFORMATION: antiHER2 coding sequence

<400> SEQUENCE: 7
gaattcgcca ccatggagtt ttggctgagc tgggttttcc ttgttgctat tttaaaaggt        60
gtccagtgtg aggttcagct ggtggagtct ggcggtggcc tggtgcagcc aggggggctca      120 ctccgtttgt cctgtgcagc ttctggcttc aacattaaag acacctatat acactgggtg      180
cgtcaggccc cgggtaaggg cctggaatgg gttgcaagga tttatcctac gaatggttat      240
actagatatg ccgatagcgt caagggccgt ttcactataa gcgcagacac atccaaaaac      300
acagcctacc tgcagatgaa cagcctgcgt gctgaggaca ctgccgtcta ttattgttct      360
agatggggag gggacggctt ctatgctatg gactactggg gtcaaggaac cctggtcacc      420
gtctcctcgg cctccaccaa gggcccatcg gtcttccccc tggcaccctc ctccaagagc      480
acctctgggg gcacagcggc cctgggctgc ctggtcaagg actacttccc cgaaccggtg      540
acggtgtcgt ggaactcagg cgccctgacc agcggcgtgc acaccttccc ggctgtccta      600
cagtcctcag gactctactc cctcagcagc gtggtgaccg tgccctccag cagcttgggc      660
acccagacct acatctgcaa cgtgaatcac aagcccagca caccaaggt ggacaagaaa       720 gttgagccca atcttgtga caaaactcac acatgcccac cgtgcccagc acctgaactc      780
ctggggggac cgtcagtctt cctcttcccc ccaaaaccca aggacaccct catgatctcc      840
cggacccctg aggtcacatg cgtggtggtg gacgtgagcc acgaagaccc tgaggtcaag      900
ttcaactggt acgtggacgg cgtggaggtg cataatgcca agacaaagcc gcgggaggag      960
cagtacaaca gcacgtaccg tgtggtcagc gtcctcaccg tcctgcacca ggactggctg     1020
aatggcaagg agtacaagtg caaggtctcc aacaaagccc tcccagcccc catcgagaaa     1080
accatctcca aagccaaagg gcagccccga gaaccacagg tgtacaccct gcccccatcc     1140
cgggatgagc tgaccaagaa ccaggtcagc ctgacctgcc tggtcaaagg cttctatccc     1200
agcgacatcg ccgtggagtg ggagagcaat gggcagccgg agaacaacta caagaccacg     1260
cctcccgtgc tggactccga cggctccttc ttcctctaca gcaagctcac cgtggacaag     1320
agcaggtggc agcaggggaa cgtcttctca tgctccgtga tgcatgaggc tctgcacaac     1380
cactacacgc agaagagcct ctccctgtct ccgggtaaac gtaaaaggcg agctcctgtt     1440
aaacagactt tgaattttga ccttctcaag ttggcgggag acgtcgagtc caaccctggg     1500
cccatggaag ccccagctca gcttctcttc ctcctgctac tctggctccc agataccacc     1560
ggagatatcc agatgaccca gtccccgagc tccctgtccg cctctgtggg cgatagggtc     1620
accatcacct gccgtgccag tcaggatgtg aatactgctg tagcctggta tcaacagaaa     1680
ccaggaaaag ctccgaaact actgatttac tcggcatcct tcctctactc tggagtccct     1740
tctcgcttct ctggatccag atctgggacg gatttcactc tgaccatcag cagtctgcag     1800
ccggaagact tcgcaactta ttactgtcag caacattata ctactcctcc cacgttcgga     1860
```

| | |
|---|---|
| cagggtacca aggtggagat caaaactgtg gctgcaccat ctgtcttcat cttcccgcca | 1920 |
| tctgatgagc agttgaaatc tggaactgcc tctgttgtgt gcctgctgaa taacttctat | 1980 |
| cccagagagg ccaaagtaca gtggaaggtg gataacgccc tccaatcggg taactcccag | 2040 |
| gagagtgtca cagagcagga cagcaaggac agcacctaca gcctcagcag cacccctgacg | 2100 |
| ctgagcaaag cagactacga gaaacacaaa gtctacgcct gcgaagtcac ccatcagggc | 2160 |
| ctgagctcgc ccgtcacaaa gagcttcaac aggggagagt gttgataagt cgac | 2214 |

<210> SEQ ID NO 8
<211> LENGTH: 20
<212> TYPE: DNA
<213> ORGANISM: artificial sequence
<220> FEATURE:
<223> OTHER INFORMATION: primer

<400> SEQUENCE: 8

| | |
|---|---|
| ggctgtccta cagtcctcag | 20 |

<210> SEQ ID NO 9
<211> LENGTH: 20
<212> TYPE: DNA
<213> ORGANISM: artificial sequence
<220> FEATURE:
<223> OTHER INFORMATION: primer

<400> SEQUENCE: 9

| | |
|---|---|
| ttgtccacct tggtgttgct | 20 |

<210> SEQ ID NO 10
<211> LENGTH: 1176
<212> TYPE: DNA
<213> ORGANISM: artificial sequence
<220> FEATURE:
<223> OTHER INFORMATION: herinCAR coding sequence comprising
    CD20-Rituxan molecular brake

<400> SEQUENCE: 10

| | |
|---|---|
| gaattcgcca ccatggagtt ttggctgagc tgggttttcc ttgttgctat tttaaaaggt | 60 |
| gtccagtgta acatatacaa ctgtgaacca gctaatccct ctgagaaaaa ctccccatct | 120 |
| acccaatact gttacagcat acaaggtgga ggtggaggtg gaggtggagg tggtacccac | 180 |
| tcactgcccc cgaggccagc tgcagttcct gtccctctgc gcatgcagcc tggcccagcc | 240 |
| caccctgtcc tatccttcct cagaccctct tgggacctag tctctgcctt ctactctcta | 300 |
| cccctggccc ccctcagccc tacaagtgtc cctatatccc ctgtcagtgt ggggaggggc | 360 |
| ccggaccctg atgctcatgt ggctgttgac ctgtcccgt atgaaggcga gcccaaatct | 420 |
| tgtgacaaaa ctcacacatg cccaccgtgc ccagcacctg agttcgtgcc ggtcttcctg | 480 |
| ccagcgaagc ccaccacgac gccagcgccg cgaccaccaa caccggcgcc caccatcgcg | 540 |
| tcgcagcccc tgtccctgcg cccagaggcg tgccggccag cggcgggggg cgcagtgcac | 600 |
| acgaggggc tggacttcgc ctgtgatatc tacatctggg cgcccctggc cgggacttgt | 660 |
| ggggtccttc tcctgtcact ggttatcacc ctttactgca accacaggag taagaggagc | 720 |
| aggctcctgc acagtgacta catgaacatg actccccgcc gccccgggcc cacccgcaag | 780 |
| cattaccagc cctatgcccc accacgcgac ttcgcagcct atcgctccag agtgaagttc | 840 |
| agcaggagcg cagacgcccc cgcgtaccag cagggccaga accagctcta taacgagctc | 900 |
| aatctaggac gaagagagga gtacgatgtt ttggacaaga cgtggccg ggaccctgag | 960 |

```
atgggggga aagccgagaag gaagaaccct caggaaggcc tgtacaatga actgcagaaa    1020
gataagatgg cggaggccta cagtgagatt gggatgaaag gcgagcgccg gaggggcaag    1080
gggcacgatg gcctttacca gggtctcagt acagccacca aggacaccta cgacgccctt    1140
cacatgcagg ccctgccccc tcgctgataa gtcgac                              1176
```

<210> SEQ ID NO 11
<211> LENGTH: 2745
<212> TYPE: DNA
<213> ORGANISM: artificial sequence
<220> FEATURE:
<223> OTHER INFORMATION: herinCAR-PD1 coding sequence

<400> SEQUENCE: 11

```
gaattcgcca ccatggagtt ttggctgagc tgggttttcc ttgttgctat tttaaaaggt      60
gtccagtgta acatatacaa ctgtgaacca gctaatccct ctgagaaaaa ctccccatct     120
acccaatact gttacagcat acaaggtgga ggtggaggtg gaggtggagg tggtacccac     180
tcactgcccc cgaggccagc tgcagttcct gtccctctgc gcatgcagcc tggcccagcc     240 cacccctgtcc tatccttcct cagaccctct gggacctag tctctgcctt ctactctcta    300
ccctggcccc cctcagcccc tacaagtgtc cctatatccc ctgtcagtgt ggggaggggc    360
ccggaccctg atgctcatgt ggctgttgac ctgtccggt atgaaggcga cccaaatct      420 tgtgacaaaa ctcacacatg cccaccgtgc ccagcacctg agttcgtgcc ggtcttcctg    480
ccagcgaagc ccaccgac gccagcgccg cgaccaccaa caccggcgcc caccatcgcg      540
tcgcagcccc tgtccctgcg cccagaggcg tgccggccag cggcgggggg cgcagtgcac    600 acgaggggc tggacttcgc ctgtgatatc tacatctggg cgcccctggc cgggacttgt     660
ggggtccttc tcctgtcact ggttatcacc ctttactgca accacaggag taagaggagc    720
aggctcctgc acagtgacta catgaacatg actccccgcc gccccgggcc caccccgaag    780
cattaccagc cctatgcccc accacgcgac ttcgcagcct atcgctccag agtgaagttc    840
agcaggagcg cagacgcccc cgcgtaccag cagggccaga accagctcta taacgagctc    900
aatctaggac gaagagagga gtacgatgtt ttggacaaga cgtggccg ggaccctgag       960 atgggggga aagccgagaag gaagaaccct caggaaggcc tgtacaatga actgcagaaa    1020
gataagatgg cggaggccta cagtgagatt gggatgaaag gcgagcgccg gaggggcaag    1080
gggcacgatg gcctttacca gggtctcagt acagccacca aggacaccta cgacgccctt    1140
cacatgcagg ccctgccccc tcgccgtaaa aggcgagctc tgttaaaaca gactttgaat    1200
tttgaccttc tcaagttggc gggagacgtc gagtccaacc tgggcccat ggaagcccca     1260 gctcagcttc tcttcctcct gctactctgg ctcccagata ccaccggaca ggtgcagctg    1320
gtgcagtccg gcgtggaggt gaagaagcct ggcgcctccg tcaaggtgtc ctgtaaggcc    1380
tccggctaca ccttcaccaa ctactacatg tactgggtgc ggcaggcccc aggccaggga    1440
ctggagtgga tgggcggcat caaccccttcc aacggcggca ccaacttcaa cgagaagttc    1500
aagaaccggg tgaccctgac caccgactcc tccaccacaa ccgcctacat ggaactgaag    1560
tccctgcagt cgacgacac cgccgtgtac tactgcgcca gcgggacta ccggttcgac      1620 atgggcttcg actactgggg ccagggcacc accgtgaccg tgtcctccgg tggaggcggt    1680
tcaggcggag gtggcagcgg cggtggcggg tcggaaattg tgttgacaca gtctccagcc    1740 acctgtctt tgtctccagg ggaaagagcc accctctcct gcagggccag caaaggtgtc    1800
```

-continued

| | |
|---|---|
| agtacatctg gctatagtta tttgcactgg tatcaacaga aacctggcca ggctcccagg | 1860 |
| ctcctcatct atcttgcatc ctacctagaa tctggcgtcc cagccaggtt cagtggtagt | 1920 |
| gggtctggga cagacttcac tctcaccatc agcagcctag agcctgaaga ttttgcagtt | 1980 |
| tattactgtc agcacagcag ggaccttccg ctcacgttcg gcggagggac caaagtggag | 2040 |
| atcaaagagt ccaaatatgg tccccatgc ccaccatgcc cagcacctga gttcctgggg | 2100 |
| ggaccatcag tcttcctgtt ccccccaaaa cccaaggaca ctctcatgat ctcccggacc | 2160 |
| cctgaggtca cgtgcgtggt ggtggacgtg agccaggaag accccgaggt ccagttcaac | 2220 |
| tggtacgtgg atggcgtgga ggtgcataat gccaagacaa agccgcggga ggagcagttc | 2280 |
| aacagcacgt accgtgtggt cagcgtcctc accgtcctgc accaggactg gctgaacggc | 2340 |
| aaggagtaca agtgcaaggt ctccaacaaa ggcctcccgt cctccatcga gaaaaccatc | 2400 |
| tccaaagcca aagggcagcc ccgagagcca caggtgtaca ccctgccccc atcccaggag | 2460 |
| gagatgacca agaaccaggt cagcctgacc tgcctggtca aaggcttcta ccccagcgac | 2520 |
| atcgccgtgg agtgggagag caatgggcag ccggagaaca actacaagac cacgcctccc | 2580 |
| gtgctggact ccgacggctc cttcttcctc tacagcaggc taaccgtgga caagagcagg | 2640 |
| tggcaggagg ggaatgtctt ctcatgctcc gtgatgcatg aggctctgca caaccactac | 2700 |
| acacagaaga gcctctccct gtctctgggt aaatgataag tcgac | 2745 |

<210> SEQ ID NO 12
<211> LENGTH: 21
<212> TYPE: DNA
<213> ORGANISM: artificial sequence
<220> FEATURE:
<223> OTHER INFORMATION: primer

<400> SEQUENCE: 12

| | |
|---|---|
| cagtgagatt gggatgaaag g | 21 |

<210> SEQ ID NO 13
<211> LENGTH: 19
<212> TYPE: DNA
<213> ORGANISM: artificial sequence
<220> FEATURE:
<223> OTHER INFORMATION: primer

<400> SEQUENCE: 13

| | |
|---|---|
| gaagggcgtc gtaggtgtc | 19 |

<210> SEQ ID NO 14
<211> LENGTH: 2250
<212> TYPE: DNA
<213> ORGANISM: artificial sequence
<220> FEATURE:
<223> OTHER INFORMATION: herinCAR-CD28 coding sequence

<400> SEQUENCE: 14

| | |
|---|---|
| gaattcgcca ccatggagtt tggctgagc tgggttttcc ttgttgctat tttaaaaggt | 60 |
| gtccagtgta acatatacaa ctgtgaacca gctaatccct ctgagaaaaa ctccccatct | 120 |
| acccaatact gttacagcat acaaggtgga ggtggaggtg gaggtggagg tggtacccac | 180 |
| tcactgcccc cgaggccagc tgcagttcct gtccctctgc gcatgcagcc tggcccagcc | 240 |
| cacccctgtcc tatccttcct cagaccctct tgggacctag tctctgcctt ctactctcta | 300 |
| cccctggccc ccctcagccc tacaagtgtc cctatatccc ctgtcagtgt ggggagggc | 360 |
| ccggaccctg atgctcatgt ggctgttgac ctgtcccggt atgaaggcga gcccaaatct | 420 |

-continued

```
tgtgacaaaa ctcacacatg cccaccgtgc ccagcacctg agttcgtgcc ggtcttcctg      480
ccagcgaagc ccaccacgac gccagcgccg cgaccaccaa caccggcgcc caccatcgcg      540
tcgcagcccc tgtccctgcg cccagaggcg tgccggccag cggcgggggg cgcagtgcac      600
acgagggggc tggacttcgc ctgtgatatc tacatctggg cgcccctggc cgggacttgt      660
ggggtccttc tcctgtcact ggttatcacc ctttactgca accacaggag taagaggagc      720
aggctcctgc acagtgacta catgaacatg actccccgcc gccccgggcc cacccgcaag      780
cattaccagc cctatgcccc accacgcgac ttcgcagcct atcgctccag agtgaagttc      840
agcaggagcg cagacgcccc cgcgtaccag cagggccaga accagctcta taacgagctc      900
aatctaggac gaagagagga gtacgatgtt ttggacaaga gacgtggccg ggaccctgag      960 atgggggggaa agccgagaag gaagaaccct caggaaggcc tgtacaatga actgcagaaa     1020
gataagatgg cggaggccta cagtgagatt gggatgaaag gcgagcgccg gaggggcaag     1080
gggcacgatg gcctttacca gggtctcagt acagccacca aggacaccta cgacgccctt     1140
cacatgcagg ccctgccccc tcgccgtaaa aggcgagctc ctgttaaaca gactttgaat     1200
tttgaccttc tcaagttggc gggagacgtc gagtccaacc tgggcccat ggagttttgg      1260 ctgagctggg ttttccttgt tgctatttta aaaggtgtcc agtgtcaggt gcagctggtg     1320
cagtctgggg ctgaggtgaa gaagcctggg gcctcagtga aggtctcctg caaggcttct     1380
ggatacacct tcaccagcta ctatatacac tgggtgcgac aggcccctgg acaagggctt     1440
gagtggattg gatgtatttta tcctggaaat gtcaatacta actataatga gaagttcaag     1500
gacagggcca ccctgaccgt agacacgtcc atcagcacag cctacatgga gctgagcagg     1560
ctgagatctg acgacacggc cgtgtatttc tgtacaagat cacactacgg cctcgactgg     1620
aacttcgatg tctggggcca agggaccacg gtcaccgtct cctcaggtgg aggcggttca     1680
ggcggaggtg gcagcggcgg tggcgggtcg gacatccaga tgacccagtc tccatcctcc     1740
ctgtctgcat ctgtaggaga cagagtcacc atcacttgcc atgccagtca aaacatttat     1800
gtttggttaa ctggtatca gcagaaacca gggaaagccc ctaagctcct gatctataag      1860
gcttccaacc tgcacacagg ggtcccatca aggttcagtg gcagtggatc tgggacagat     1920
ttcactctca ccatcagcag tctgcaacct gaagattttg caacttacta ctgtcaacag     1980
ggtcaaactt atccgtacac gttcggcgga gggaccaagg tggagatcaa aattgaagtt     2040
atgtatcctc ctccttacct agacaatgag aagagcaatg gaaccattat ccatgtgaaa     2100
gggaaacacc tttgtccaag tcccctattt cccggacctt ctaagccctt tgggtgctg      2160 gtggtggttg gtggagtcct ggcttgctat agcttgctag taacagtggc ctttattatt     2220
ttctgggtga ggagtaagtg ataagtcgac                                      2250
```

KILLER CELL CAPABLE OF EFFICIENTLY AND STABLY EXPRESSING ANTIBODY, AND USES THEREOF

CROSS-REFERENCE TO RELATED APPLICATIONS:

This application is a Submission under 35 U.S.C. § 371 for U.S. National Stage Patent Application of, and claims priority to, International Application Number PCT/CN2017/088955 entitled Killer Cell Capable of Efficiently and Stably Expressing Antibody, and Uses Thereof, filed Jun. 19, 2017, which is related to and claims priority to Chinese Patent Number 201610443886.6, filed Jun. 20, 2016, the entirety of all of which are incorporated herein by reference.

TECHNICAL FIELD

The present application is filed with a Sequence Listing as a text file, in computer readable form, via EFS-Web. The Sequence Listing is provided as a file entitled 1777-18PUS_Sequence_Listing.txt created on Mar. 25, 2020, which is 17,105 bytes in size. The information in computer readable form is incorporated herein by reference in its entirety.

The invention belongs to the field of cytobiology and oncology, and particularly relates to a killer cell capable of efficiently and stably expressing an antibody and uses thereof.

BACKGROUND TECHNOLOGY

Cancer has now become the leading human health killer. Fast life rhythm, tremendous working pressure, unhealthy diet habit, and bad environment are all cancer inducing factors, and lead to a remarkably increased incidence of cancer with younger incidence age. At present, traditional treatment methods have reached to a bottleneck, and there is a need to explore more effective treatment methods to improve the survival rate and the living quality of cancer patients. Immunotherapy for malignant tumors rapidly develops in recent years and achieves remarkable clinical curative effects. In 2011, both Nature and the top magazine in clinical oncology JCO published review articles with the same title "Cancer immunotherapy comes of age" (Nature. 2011, 480 (7378): 480; J Clin Oncol. 2011; 29 (36): 4828), respectively. A new peak of tumor immune cell therapy research has come. In the future, it is possible to occupy a pivotal position in tumor therapy.

"Immunity" can be classified into cellular immunity and humoral immunity, which have distinct manners in killing tumors or viruses. Cellular immunity removes foreign substances by the direct effects imposed by cells, which is a participant of an immune response in the body and also an executor of an immune function. At present, the effector immune cells used for clinical treatment, namely the killer immune cells, mainly comprise natural killer cells (nature killer, NK), lymphokine activated killer cell (LAK), cytokine activated killer cells (CIK), cytokine-activated killer cells stimulated by dendritic cells (DC-CIK), cytotoxic T-lymphocyte (CTL), γδT cell, tumor infiltrating lymphocyte (TIL), CD3AK cells (anti-CD3 monoclonal antibody killer cells) and the like. These cells do not express antibodies and directly kill or act through antibody dependent cell-mediated cytotoxicity effect (ADCC).

Humoral immunity is mediated by antibodies, and antibodies in human body are generated by B lymphocytes. In 1997, the first monoclonal antibody for clinical cancer treatment, namely an anti-human CD20 (rituximab) was approved by FDA. With the development of antibody technology, till now there are more than 100,000 antibodies reported in the world, among which more than 1,000 are genetically engineered antibodies, and more than 200 are humanized antibodies. Till March 2016, FDA has approved 50 antibodies for marketing, wherein 26 are used for tumor therapy. These antibodies not only act directly on tumor cells, but also act on immune cells and take effect indirectly.

However, although effector immune cells have certain anti-tumor effects, the clinical treatment effect thereof is limited; while the penetrability of macromolecular antibodies to the solid tumors is insufficient, and systemic administration can cause systematic adverse reactions. For example, the HER2 monoclonal antibody has cardiac toxicity, and the PD1 antibody breaks the body immune balance so that autoimmune diseases can be caused. In addition, due to the fact that the antibody drug involves complicated in vitro production and preparation processes, with high purity requirement and large dosage, the medication cost is high. Therefore, if the cellular immunity effector cells keep the cell killing toxicity while being able to efficiently express antibody with anti-tumor activity, the problems that the immune treatment effect of cells is insufficient and a macromolecular antibody is difficult to enter into solid tumors will be simultaneously overcome, with the treatment cost reduced. Under the effect of chemokines, the cells with both cell killing toxicity and high-level expression of antibodies can actively enter into tumor tissue via cytomorphosis, so that local high-level expression of antibody in the tumor tissue can be achieved, and the side effects caused by systemic administration can be avoided. Meanwhile, due to the co-existence of the antibody and the cytotoxic cell killing immune cells, the antibody acting on the immune cells (such as HER2 antibody Herceptin) can induce strong ADCC effect and CDC effect to efficiently kill tumor cells. Moreover, the antibody acting on T cells (such as PD1 antibody Keytruda) can prevent the inhibitory effects of tumor microenvironment on the re-infused effector T cells, making them continuously exert a therapeutic effect.

Although it has been reported that exogenous genes are transduced into, for example, NK cells or T cells, currently the conventionally used gene transfection vector systems are low in transfection efficiency when applied to effector immune cells with cell killing toxicity, or are difficult to express exogenous genes in the cells at high level. The adenovirus vector (non-integrated) can mediate short-time high-efficiency expression of exogenous genes in NK cells or T cells, but the proliferation speed of the activated NK cells or T cells is so fast that the exogenous gene expression cassette carried can be rapidly lost in cell passaging, and the expression is difficult to last. The integration of an exogenous gene into NK cell or T cell genome can be mediated by a retrovirus or a lentivirus, for which stable expression can be realized theoretically. However, an antibody contains both light chains and heavy chains with long coding sequences and large molecular weight, making it very difficult to package and prepare retrovirus or lentivirus with full-length antibody expression cassette and to express the antibody efficiently. They can only be used to express the structurally simple single-chain antibody (lacking Fc segment, incomplete in function and short in half-life). Therefore, there is no report about transgenic cells that have cell

SUMMARY OF THE INVENTION

The first aspect of the invention provides a transgenic killer cell, wherein acoding sequence of an antibody with human Fc segment is stably integrated in the genome of the killer cell, or the genome of the killer cell comprises an expression cassette comprising a coding sequence of a chimeric antigen receptor and a single-chain antibody of interest, wherein both ends of the expression cassette comprise inverted terminal repeat sequences of the transposon.

In one or more embodiments, the amount of the antibody expressed within 48 hours per million of the killer cells is more than 2 μg.

In one or more embodiments, the transposon is selected from the group consisting of piggybac, sleeping beauty, frog prince, Tn5 and Ty; preferably, the transposon is piggybac.

In one or more embodiments, the killer cells are selected from the group consisting of: cytokine activated killer cells, dendritic cell stimulated cytokine-activated killer cells, cytotoxic T lymphocytes, γδT cells, natural killer cells, NKT cells, tumor infiltrating lymphocytes, lymphokine-activated killer cells, anti-CD3 monoclonal antibody killer cells and genetically modified CAR-T/CAR-NK/TCR-T cells: preferably, the killer cells are T cells, NK cells or CAR-T cells.

In one or more embodiments, the killer cells further comprise a molecular brake.

In one or more embodiments, the molecular brake is a membrane antigen that can be recognized by a commercially available antibody drug.

In one or more embodiments, the membrane antigen is selected from the group consisting of: CD11a, CD15, CD19, CD20, CD25, CD44, CD47, CD52, EGFR, ERBB2, ERBB3, ERBB4, VEGFR1, VEGFR2, EpCAM, MSLN, GPIIb/IIIa, α4 integrin and α4β7 integrin; preferably, the membrane antigen is CD20.

In one or more embodiments, the antibody is an anti-tumor or anti-virus antibody.

In one or more embodiments, the antibody is selected from the group consisting of: immune check point antibody, T cell co-stimulation signal antibody, anti-angiogenic antibody, antibody against tumor cell growth factor receptor, antibody against tumor cell membrane antigen and antibody against viruses.

In one or more embodiments, the antibody is directed to one or more of the following antigens: PD-1, CTLA4, PDL1, PDL2, PDL3, TIM3, LAG3, CD28, CD137, CD40, CD40L, CD47, CD19, CD20, CEA, GD2 (also known as B4GALNT1, β-1,4-acetyl-aminogalactosyl transferase 1), FR (flavin reductase), PSMA (prostate specific membrane antigen), gp100 (PMEL premelanosome protein), CA9 (carbonic anhydrase IX), CD171/L1-CAM, IL-13Rα2, MART-1 (also known as melan-A), ERBB2, NY-ESO-1 (also known as CTAG1B, cancer/testicle antigen 1B), MAGE (melanoma associated antigen E1) family proteins, BAGE (B melanoma antigen family) family proteins, GAGE (Growth Hormone Releasing Factor) family proteins, α-fetoprotein (AFP), MUC1 (mucin 1, cell-surface related), CD22, CD23, CD30, CD33, CD44v7/8, CD70, VEGFR1, VEGFR2, IL-11Rα, EGP-2, EGP-40, FBP, GD3 (also known as ST8SIA1, ST8α-N-acetyl-ceramide α-2,8-sialic acid convertase 1), PSCA (prostate stem cell antigen), FSA (also known as KIAA1109). PSA (also known as KLK3, Kallikrein-related peptidase 3), HMGA2, Fetal acetylcholine receptor, LeY (also known as FUT3), EpCAM, MSLN (mesothelin), IGFR1, EGFR, EGFRvIII, ERBB3, ERBB4, CA125 (also known as MUC16, mucin 16, cell-surface related), CA15-3, CA19-9, CA72-4, CA242, CA50, CYFRA21-1, SCC (also known as SERPINB3), AFU (also known as FUCA1), EBV-VCA, POA (also known as VDR, vitamin D (1,25-dihydrovitamin D3) receptor), β2-MG (β-2-Microglobulin) and PROGRP (GRP, Gastrin releasing peptide), HBV, and HIV.

In one or more embodiments, the antibody is a PD-1 antibody or a HER2 antibody.

In one or more embodiments, the transgenic killer cells are transformed with nucleic acid constructs A and B, or nucleic acid construct C as shown below:

Nucleic acid construct A: comprising a transposon's 5'-inverted terminal repeat sequence (5'ITR), a coding sequence of an antibody comprising human Fc segment and a promoter controlling the expression of such a nucleic acid sequence, a polyA tailing signal sequence and a transposon's 3'-inverted terminal repeat sequence (3' ITR);

Nucleic acid construct B: comprising a transposon's 5'-inverted terminal repeat sequence (5'ITR), a coding sequence of molecular brake and a promoter controlling the expression of such a nucleic acid sequence, a polyA tailing signal sequence and a transposon's 3'-inverted terminal repeat sequence (3' ITR), a transposase coding sequence and optionally, a promoter controlling the expression of the coding sequence of the transposase;

Nucleic acid construct C: comprising a transposon's 5'-inverted terminal repeat sequence (5'ITR), a nucleic acid sequences encoding optionally a molecular brake, a chimeric antigen receptor (CAR) and an antigen-binding fragment of a single-chain antibody of interest, and a promoter controlling the expression of such a nucleic acid sequence, a polyA tailing signal sequence, a transposon's 3'-inverted terminal repeat sequence (3' ITR), a transposase coding sequence and a promoter controlling the expression of the coding sequence of the transposase.

In one or more embodiments, one or more methods selected from virus transduction, microinjection, particle bombardment, gene gun transformation and electroporation are employed to transform the nucleic acid construct(s) into the cells, preferably, electroporation is used.

The second aspect of the invention provides a pharmaceutical composition, wherein the pharmaceutical composition comprises the transgenic killer cells as described herein and a pharmaceutically acceptable excipient.

The third aspect of the invention provides the use of the transgenic killer cells or the pharmaceutical composition described herein, wherein the use is selected from the group consisting of: preparation of a medicine for inhibiting tumor cell growth, preparation of a medicine for inhibiting virus growth, preparation of a medicine for treating tumors, preparation of a medicament for treating viral infectious diseases, preparation of a medicament for treating bacterial infectious diseases and preparation of a medicament for treating autoimmune diseases:

wherein the tumor is selected from the group consisting of liver cancer, lung cancer, colon cancer, pancreatic cancer, gastric cancer, breast cancer, nasopharyngeal carcinoma, lymphoma, ovarian cancer, bladder cancer, prostate cancer and head and neck tumors.

DETAILED EMBODIMENTS

Figure 1:
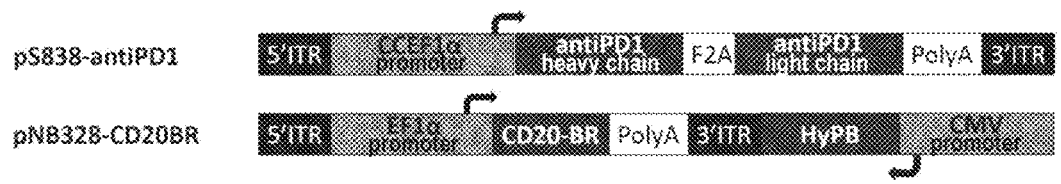
FIG. 1: A schematic diagram of the expression cassette of PD-1 antibody. ITR is a transposon's inverted terminal repeat sequence; HyPB is a piggybac transposase.

Some terms involved in the invention are explained below.

In the present invention, the term "expression cassette" refers to the complete elements required to express a gene, including promoter, gene coding sequence and polyA tailing signal sequence.

The term "coding sequence" is defined herein as a part of a nucleic acid sequence that directly determines the amino acid sequence of its protein product. The boundaries of a coding sequence are usually determined by a ribosome binding site closely adjacent to the upstream of open reading frame at mRNA 5'end (for prokaryotic cells) and a transcriptional termination sequence closely adjacent to the downstream of the open reading frame at mRNA 3'end. The coding sequence can include, but is not limited to, DNA, cDNA and recombinant nucleic acid sequences.

The term "agonistic antibody" refers to an antibody that can agonise/activate a specific type of immune response when present. The term "inhibitory antibody" refers to an antibody that can inhibit a specific type of immune response when present. The agonistic antibody or inhibitory antibody can be the full length sequence of an antibody or a functional fragment thereof. In one or more embodiments, the agonistic antibody or the inhibitory antibody may be selected from: Fab, Fab', F (ab') 2, Fv, scfv and scfv-Fc.

The term "antigen-binding fragment" (Fab) refers to a peptide fragment located at the end of the two arms of the "Y" structure of an antibody molecule, which consists of amino acid sequences of hypervariable region and determines the antigen-binding specificity of the antibody.

The term "Fc" refers to the crystallizable fragment of an antibody, which means a peptide fragment located at the terminal of the "Y" handle structure of the antibody, comprising peptide segments of antibody heavy chain constant regions CH2 and CH3, which is the part of an antibody that interacts with effector molecule or cell.

The term "antigen epitope", also known as antigenic determinant (AD), refers to a special chemical moiety in an antigen which determines the antigen specificity. In general, a polypeptide epitope contains 5-6 amino acid residue antigen epitopes, which can be recognized by specific antibodies. The specificity of the antigen is determined by the nature, the number and the spatial configuration of the antigen epitopes. According to difference in amino acid continuity of the antigen epitopes, the antigen epitopes can be classified into linear epitopes and spatial epitopes. The linear epitope is an epitope consisting of sequentially proximate amino acids, and the space epitope is an epitope formed by several amino acids that are not sequentially proximate, but are in spatial vicinity.

The term "co-stimulating molecule" refers to a molecule that exists on the surface of an antigen-presenting cell, which is capable of binding to co-stimulating molecular receptors on Th cells to generate synergistic stimulation signals. The proliferation of lymphocyte not only requires binding of the antigen, but also the receiving of the co-stimulating molecule signal. The transmission of co-stimulation signal to T cell is mainly by the binding of co-stimulating molecules CD80 and CD86 expressed on the surface of an antigen-presenting cell to CD28 molecule on the surface of T cells. The receiving of co-stimulation signal by B cells can be mediated by common pathogen components such as LPS, or by complement component, or CD40L on activated antigen-specific Th cell surface.

The term "linker" or hinge is a polypeptide fragment that links different proteins or polypeptides, and the purpose of which is to keep the independent spatial conformation of the linked protein or polypeptide to maintain the function or activity of the protein or polypeptide.

The term "specific binding" refers to the reaction between an antibody or antigen binding fragment and an antigen which it recognizes. In certain embodiments, an antibody specifically binding to a certain antigen (or an antibody that is specific to a certain antigen) means that the antibody binds to the antigen with an affinity (Kd) of less than about $10^{-5}M$, such as less than about $10^{-6}M$, $10^{-7}M$, $10^{-8}M$, $10^{-9}M$ or $10^{-10}M$ or less. "Specific recognition" has a similar meaning.

The term "a pharmaceutically acceptable excipient" refers to a carrier and/or an excipient that are pharmacologically and/or physiologically compatible with a subject and active ingredient(s), which is well known in the art (see, for example, Remington's Pharmaceutical Sciences, Gennaro A R Ed., $19^{th}$ edition, Pennsylvania: Mack Publishing Company, 1995), including but not limited to, pH adjusting agent, surfactant, adjuvant, ion strength enhancer. For example, the pH adjusting agent includes, but is not limited to, phosphate buffer; the surfactant includes, but is not limited to, cationic, anionic or non-ionic surfactant, such as Tween-80; the ion strength enhancer includes, but is not limited to, sodium chloride.

The term "an effective amount" refers to a dosage amount that can treat, prevent, reduce and/or alleviate the disease or condition of the present invention in a subject.

The term "disease and/or condition" refers to a physical state of the subject, wherein the physical state is related to the diseases and/or conditions of the invention.

The term "subject" may refer to a patient or other animals, particularly a mammal, such as a human, a dog, a monkey, a cow, a horse and the like, that receives the pharmaceutical composition of the invention for treating, preventing, reducing and/or alleviating the diseases or conditions of the present invention.

A type of nucleic acid construct (also referred to herein as "nucleic acid construct A") is provided herein. Such a type of nucleic acid construct comprises transposon's 5' inverted terminal repeat sequence (5'ITR), a nucleic acid sequence of interest and optionally, a promoter controlling the expression of said nucleic acid of interest, a polyA tailing signal sequence and a transposon's 3' inverted terminal repeat sequence (3'ITR).

Also provided herein is another type of nucleic acid construct (also referred to herein as "nucleic acid construct B"). Such a type of nucleic acid construct comprises transposon's 5' inverted terminal repeat sequence (5' ITR), optionally a nucleic acid sequence encoding a molecular brake and optionally a promoter controlling the expression of said nucleic acid sequence, a polyA tailing signal sequence, a transposon's 3' inverted terminal repeat sequence (3' ITR), a transposase coding sequence and optionally a promoter controlling the expression of the coding sequence of the transposase.

Also provided herein is another type of nucleic acid construct (also referred to herein as "nucleic acid construct C"). Such a type of nucleic acid construct comprises a transposon's 5' inverted terminal repeat sequence (5' ITR), a nucleic acid sequences encoding optionally a molecular brake, a chimeric antigen receptor (CAR) and inhibitory antibody or agonistic antibody (such as a single-chain antibody of interest) and a promoter controlling the expression of said nucleic acid sequence, a polyA tailing signal sequence, a transposon's 3' inverted terminal repeat sequence (3' ITR), a transposase coding sequence and optionally a promoter controlling the expression of the coding sequence of the transposase.

As used herein, "a nucleic acid sequence of interest" may be a nucleic acid sequence encoding various functional proteins known in the art. Such functional proteins include various antibodies, in particular constant regions and/or variable regions of the antibodies, including but not limited to heavy chain constant region, light chain constant region, heavy chain variable region and light chain variable region. In some embodiments, the nucleic acid sequence of interest encodes a full length sequence of the Fc segment of an antibody or the functional fragment thereof. In some embodiments, the nucleic acid sequence of interest encodes a heavy chain constant region (e.g., Fc) and a light chain of the antibody. In certain embodiments, the nucleic acid sequence of interest encodes the full-length heavy-chain sequence and the full-length light-chain sequence of the antibody. In some embodiments, nucleic acid sequences encoding heavy chain segment and light chain segment can be linked by commonly used linker sequences (such as the coding sequence of Furin 2A). "Segment" as used herein refers to the fundamental structural unit of an antibody, such as the $C_H1$, $C_H2$, $C_H3$, $C_L$, $V_L$, $V_H$ parts of an antibody and the like.

The antibodies of interest may be human antibodies, including human-murine chimeric antibodies and humanized antibodies. Antibodies of interest may be selected from an immune check point antibody, a T cell co-stimulation signal antibody, an anti-angiogenic antibody, an antibody against tumor cell growth factor receptor, and an antibody against tumor cell membrane antigen. In some embodiments, the antibody of interest may be an antibody against one or more of the following antigens: PD-1, CTLA4, PDL1, PDL2, PDL3, TIM3. LAG3, CD28, CD137, CD40, CD40L, CD47, CD19, CD20, CEA, GD2 (also known as B4GALNT1, β1,4-acetyl-aminogalactosyl transferase 1), FR (flavin reductase). PSMA (prostate specific membrane antigen), gp100 (PMEL premelanosome protein), CA9 (carbonic anhydrase IX), CD171/L1-CAM, IL-13Rα2. MART-1 (also known as melan-A), ERBB2, NY-ESO-1 (also known as CTAG1B, cancer/testicle antigen 1B), MAGE (melanoma associated antigen E1) family proteins, BAGE (B melanoma antigen family) family proteins, GAGE (Growth Hormone Releasing Factor) family proteins, α-fetoprotein (AFP), MUC1 (mucin 1, cell-surface related), CD22, CD23, CD30, CD33, CD44v7/8, CD70, VEGFR1, VEGFR2, IL-11Rα, EGP-2, EGP-40, FBP, GD3 (also known as ST8SIA1, ST8α-N-acetyl-ceramide α-2,8-sialic acid convertase 1), PSCA (prostate stem cell antigen), FSA (also known as KIAA1109), PSA (also known as KLK3, Kallikrein-related peptidase 3), HMGA2, Fetal acetylcholine receptor, LeY (also known as FUT3). EpCAM, MSLN (mesothelin), IGFR1, EGFR, EGFRvIII, ERBB3, ERBB4, CA125 (also known as MUC16, mucin 16, cell-surface related), CA15-3, CA19-9, CA72-4, CA242, CA50, CYFRA21-1, SCC (also known as SERPINB3), AFU (also known as FUCA1), EBV-VCA, POA (also known as VDR, vitamin D (1,25-dihydro vitamin D3) receptor), β2-MG (β-2-Microglobulin) and PROGRP (GRP, Gastrin releasing peptide), HBV, and HIV. In some embodiments, the antibody is an antibody acting on T cell itself, and after being expressed by T cells, it can protect T cells from being inhibited by tumor microenvironment and allow the T cells to locally express antibodies in tumor with reduced toxic side-effects. In other embodiments, the antibody is antibody acting on tumor cells, which after being expressed by killer cells such as NK cells, can, through guidance of the antibody, produce a synergistic ADCC effect with the killer cells. In some embodiments, the antibody is a secretory antibody. In other embodiments, the antibody is a membrane anchoring antibody. In one or more embodiments, the antibody is PD-1 antibody or HER2 antibody.

The term "single chain antibody" (scFv) refers to an antibody fragment formed by linking the amino acid sequences of antibody light chain variable region ($V_L$ region) and heavy chain variable region (Vii region) with hinge, which has antigen-binding ability. In certain embodiments, a single chain antibody of interest (scFv) is derived from the antibodies of interest described above and comprises the respective heavy chain variable region and light chain variable region of the respective antibodies of interest, or consists of a heavy chain variable region, a light chain variable region and optionally a linker. The heavy chain variable region and the light chain variable region can be linked by a well-known linker, for example, a linker containing G and S. The length of the linker is generally of 15-20 amino acids. In some embodiments, the linker is $(GGGS)_n$, and n is an integer of 1 to 5. It should be understood that the nucleic acid constructs herein may encode two single chain antibodies, one exists in the shown CAR, and the other is a single-chain antibody linked to the CAR. The two single-chain antibodies can be the same or different, preferably, the two single-chain antibodies perform different antibody functions.

In certain embodiments, nucleic acid construct C of the present invention can further comprise coding sequences of the hinge region from immunoglobulin and the Fc region at a location downstream from the nucleic acid sequence encoding the inhibitory antibody (for example the single chain antibody of interest). Various types of immunoglobulins known in the art can be used, but in certain preferred embodiments, the immunoglobulin is human IgG4.

In certain embodiments, nucleic acid construct C of the present invention can further comprise extracellular hinge region and transmembrane region sequences from the antigen to which the antibody is directed at a location downstream from the nucleic acid sequence encoding an agonistic antibody (for example the single chain antibody of interest). For example, when anti-CD28 antibody is used, scFv derived from the antibody can be used and connected with CD28 extracellular hinge region and transmembrane region sequence at the downstream location thereof.

In some embodiments, the inhibitory antibody is an immune checkpoint inhibitory antibody. In certain embodiments, the inhibitory antibody is directed against one or more of the following antigens: PD-1, CTLA4, PDL1, PDL2, PDL3, TIM3, LAG3, CD47, BTLA, TIGIT, CD160, LAIRI, B7-H1, B7-1, VSIR and CD244; preferably, the inhibitory antibody is an anti-PD-1 antibody (such as an scFv-Fc). In some embodiments, the inhibitory antibody is an scFv-Fc antibody.

In some embodiments, the agonistic antibody is an agonistic antibody directed against immune co-stimulating molecules and receptors thereof. In some embodiments, the agonistic antibody is directed against one or more of the following antigens: CD28, CD137, CD134, CD40, CD40L, ICOS, HVEM, CD2, CD27, CD30, GITR, LIGHT, DR3, SLAM and CD226. Preferably, the agonistic antibody is an anti-CD28 antibody (such as an scFv). In some embodiments, the inhibitory antibody is a single chain antibody.

As used herein, "PD1" refers to a programmed death receptor 1, which has the official name of "PDCD1" in NCBI genebank and an ID number of 5133, whose cDNA sequence/protein sequence are NM_005018.2/NP_005009.2.

"ERBB2" refers to a cell growth factor receptor 2 (also called HER2), which has an official name in NCBI GeneBank of ERBB2 and an ID number of 2064. ERBB2 has five isoforms, whose cDNA sequences/proteins are NM_004448.3/NP_004439.2, NM_001005862.2/NP_001005862.1, NM_001289936.1/NP_001276865.1, NM_001289937.1/NP_001276866.1, NM_001289938.1/NP_001276867.1, respectively.

"CD20" refers to human leukocyte differentiation antigen 20, which has an official name in the NCBI GeneBank of MS4A1 and an ID No. of 931. CD20 has two isoforms whose cDNA sequences/protein sequences are NM_021950.3/NP_068769.2, NM_152866.2/NP_690605.1, respectively. When the amino acid sequence of CD20 is mentioned, it comprises the full length of the CD20 protein or the CD20 fragments with CD20 function: and also comprises fusion proteins comprising the full-length CD20 or the fragment thereof. Moreover, a skilled person in the art appreciates that, in the amino acid sequence of CD20, mutations or variations (including but not limited to substituent, deletion and/or addition) can naturally occur or can be artificially introduced, without affecting the biological function. Moreover, when a protein sequence fragment of CD20 is described, it further comprises the corresponding sequence fragment in its natural form or in an artificial variant thereof.

"CD28" refers to human leukocyte differentiation antigen 28, which has an official name CD28 and an ID number 940 in the NCBI GeneBank. CD28 has three isoforms whose cDNA sequences/protein sequences are NM_006139.3/NP_006130.1, NM_001243077.1/NP_001230006.1, NM_001243078.1/NP_001230007.1, respectively.

"Chimeric antigen receptor" (CAR) is an artificially modified receptor which can anchor the specific molecules (such as antibodies) recognizing tumor cell surface antigens to immune cells (such as T cells), so that the immune cells can recognize tumor antigens or virus antigens and kill tumor cells or virus-infected cells. Chimeric antigen receptors suitable for the present invention can be various CARs known in the art. In some embodiments, the chimeric antigen receptor is directed against one or more of the following antigens: CD19, CD20, CEA, GD2 (also known as B4GALNT1, β1,4-acetyl-aminogalactosyl transferase 1), FR (flavin reductase), PSMA (prostate specific membrane antigen), PMEL (premelanosome protein), CA9 (carbonic anhydrase IX). CD171/L1-CAM, IL-13Rα2, MART-1 (also known as melan-A). ERBB2, NY-ESO-1 (also known as CTAG1B, cancer/testicle antigen 1B), MAGE (melanoma associated antigen E1) family proteins, BAGE (B melanoma antigen family) family proteins, GAGE (Growth Hormone Releasing Factor) family proteins, AFP (α-fetoprotein), MUC1 (mucin 1, cell-surface related), CD22, CD23, CD30, CD33, CD44v7/8, CD70, VEGFR1, VEGFR2, IL-11Rα, EGP-2, EGP-40, FBP, GD3 (also known as ST8SIA1, ST8α-N-acetyl-ceramide α-2,8-sialic acid convertase 1), PSCA (prostate stem cell antigen), FSA (also known as KIAA1109), PSA (also known as KLK3, Kallikrein-related peptidase 3), HMGA2, fetal acetylcholine receptor, LeY (also known as FUT3), EpCAM, MSLN (mesothelin), IGFR1, EGFR, EGFRvIII, ERBB3, ERBB4. CA125 (also known as MUC16, mucin 16, cell-surface related), CA15-3, CA19-9, CA72-4, CA242. CA50. CYFRA21-1, SCC (also known as SERPINB3), AFU (also known as FUCA1), EBV-VCA, POA (also known as VDR, vitamin D (1,25-dihydroxy vitamin D3) receptor), 12-MG (β-2-Microglobulin) and PROGRP (GRP, Gastrin releasing peptide). Preferably, the CAR is a chimeric antigen receptor for the EGFR family.

In certain embodiments, herinCAR from CN201510812654.9 is used herein (incorporated herein by reference in its entirety).

In some embodiments, the polypeptide binding to tumor cell membrane antigen is a natural polypeptide, and is an amino acid sequence of HERIN encoded by the eighth intron Herin of human Her2 gene; preferably, the amino acid sequence is as shown in SEQ ID NO: 5 of CN201510812654.9.

In certain embodiments, the amino acid sequence of the CAR signal peptide is as shown in SEQ ID NO: 3 of CN201510812654.9.

In some embodiments, the hinge region of the CAR of the present invention is selected from one or more of the extracellular hinge region of CD8, the extracellular hinge region of CD28 and the extracellular hinge region of CD4; preferably, the extracellular hinge region of CD8. In certain embodiments, the extracellular hinge region of CD8 is as shown in SEQ ID NO: 7 of CN201510812654.9.

In some embodiments, the transmembrane region of the CAR of the present invention is selected from one or more of the transmembrane region of CD8, the transmembrane region of CD28 and the transmembrane region of CD4; preferably, the transmembrane region of CD8; preferably, the amino acid sequence of the CD8 transmembrane region is as shown in SEQ ID NO: 8 in CN201510812654.9.

In some embodiments, the intracellular signal region of the CAR of the present invention may be selected from one or more of the intracellular signal region of CD28, CD134/OX40, CD137/4-1BB, LCK, ICOS. DAP10, CD3ζ and FcεRIγ, preferably the 4-1BB intracellular signal region and CD3ζ intracellular signal region, or the CD28 intracellular signal region and the CD3ζ intracellular signal region; preferably, the 4-1BB intracellular signal region and the CD3ζ intracellular signal region have amino acid sequences as shown in SEQ ID NO:9 and SEQ ID NO: 10 of CN 201510812654.9, respectively. Preferably, the CD28 intracellular signal region and the CD3ζ intracellular signal region have amino acid sequences as shown in SEQ ID NO:11 and SEQ ID NO: 10 of CN 201510812654.9, respectively.

In certain embodiments, the antigen epitope is linked with the polypeptide binding to tumor cell membrane antigen directly or via a protein linker. Generally, the linker consists of at least two glycines, such as 2, 3, 4, 5, 6, 7, 8, 9 or 10 glycines.

In some embodiments, the chimeric antigen receptors of the present invention consist of sequentially arranged: a signal peptide, a CD20 antigen epitope, an amino acid sequence of HERIN encoded by the eighth intron Herin of human HER2 gene, a CD20 antigen epitope, a CD8 hinge region, a CD8 transmembrane region, and a 4-1BB co-stimulating peptide segment. Preferably, the amino acid sequence thereof is as shown in SEQ ID NO: 1 of CN201510812654.9.

Corresponding promoter sequence can be selected according to the selected nucleic acid sequence of interest. Examples of such promoters include, but are not limited to, EF1 alpha promoters. As described in CN201510021408.1 (the contents of which are incorporated herein by reference in their entirety), the upstream of the promoter can further comprise enhancers, such as one, any two or all three of mCMV enhancer, hCMV enhancer and CD3e enhancer.

Thus, in certain embodiments, various promoter sequences disclosed in CN201510021408.1 are used herein, including but not limited to the mCMV enhancer-containing, hCMV enhancer and EF1α promoters shown in SEQ ID NO: 1 of the application. CCEF promoter; SEQ ID NO: 2 shown CD3e containing enhancer and EF1α promoter TEF promoter; SEQ ID NO: 3 shown CD3e containing enhancers, mCMV enhancer, hCMV enhancer and promoter EF1α TCEF promoter; SEQ ID NO: 4 is shown containing mCMV enhancer, hCMV promoter and enhanced CCEFI promoter containing intron EF1α a promoter; SEQ ID NO: 5 CD3e shown containing enhancer and intron-containing a TEFI promoter of the EF1α promoter; and a TCEFI promoter comprising the CD3e enhancer, the mCMV enhancer, the hCMV enhancer, and the intron-containing EF1α promoter represented by SEQ ID NO:6.

The transposases herein can be transposases from piggybac, sleeping beauty, frog prince, Tn5 or Ty transposon systems. When transposases from different transposon systems are used, the sequences of 5'ITR and 3'ITR in the nucleic acid construct disclosed by the invention are correspondingly changed into sequences matching the transposon systems, which can be easily determined by those skilled in the art.

In certain embodiments, the transposase is a transposase from piggybac transposon system. Thus, in these embodiments, the 5' ITR sequence and 3' ITR sequence of the transposon are the 5' ITR sequence and 3' ITR sequence of the piggybac transposon, respectively. In certain embodiments, the 5' ITR sequence is as shown in SEQ ID NO: 1 of CN201510389747, which is hereby incorporated by reference in its entirety. In certain embodiments, the 3' ITR sequence is as shown in SEQ ID NO: 4 of CN201510638974.7. In certain embodiments, the piggybac transposase is a transposase comprising c-myc nuclear localization signal coding sequence. In certain embodiments, the coding sequence of piggybac transposase is as shown in SEQ ID NO: 5 of CN201510638974.7.

The promoter of the transposase coding sequence can be various promoters known in the art for controlling the expression of transposase coding sequences. In certain embodiments, the expression of transposase coding sequence is controlled by CMV promoter. The sequence of CMV promoter can be as shown in SEQ ID NO:6 of CN201510638974.7.

PolyA tailing signal sequence known in the art can be used. In certain embodiments, the polyA is from SV40. In certain embodiments, the sequence shown in SEQ ID NO: 3 of CN201510638974.7 can be used.

As used herein. "molecular brake" refers to membrane antigens that can be recognized by a commercially available antibody drug. By adding an antibody drug that recognizes the "molecular brake", cells carrying such a molecular brake can be rapidly removed, so that the treatment safety is improved. Suitable molecular brakes (membrane antigens) can be selected from the group consisting of CD11a, CD15, CD19, CD20, CD25, CD44, CD47, CD52, EGFR, ERBB2, ERBB3, ERBB4, VEGFR1, VEGFR2, EpCAM, MSLN (mesothelin), GPIIb/IIIa, α4 integrin and α4β7 integrin. In some embodiments, the membrane antigen is CD20. In certain embodiments, a linear epitope or spatial epitope of the membrane antigen can be used.

Suitable promoters can be selected for the selected membrane antigens to control the expression of said membrane antigens. In certain embodiments, the promoter is EF1α promoter. In some embodiments, the sequence of EF1α promoter is as shown in SEQ ID NO:8 of CN201510638974.7.

In certain embodiments, nucleic acid construct A disclosed herein comprises sequentially arranged: a transposon 5' inverted terminal repeat sequence (5' ITR), a promoter controlling the expression of a nucleic acid of interest, the nucleic acid sequence of interest, a polyA tailing signal sequence and a transposon 3' inverted terminal repeat sequence (3' ITR).

In certain embodiments, nucleic acid construct B disclosed herein comprises sequentially arranged: a transposon 5' inverted terminal repeat sequence (5' ITR), a promoter controlling the expression of a nucleic acid sequence encoding a molecular brake, the nucleic acid sequence encoding the molecular brake, a polyA tailing signal sequence, a transposon 3' inverted terminal repeat sequence (3' ITR), a transposase coding sequence and a promoter controlling the expression of the coding sequence of the transposase.

In certain embodiments, "nucleic acid construct C" described herein comprises sequentially arranged: a transposon 5' inverted terminal repeat sequence (5' ITR), a promoter controlling the expression of a nucleic acid sequence encoding a molecular brake, a chimeric antigen receptor (CAR) and an inhibitory antibody or an agonistic antibody (such as a single-chain antibody of interest), the nucleic acid sequences encoding the molecular brake, the chimeric antigen receptor (CAR) and the inhibitory antibody or the agonistic antibody (such as the single-chain antibody of interest), a polyA tailing signal sequence, a transposon 3' inverted terminal repeat sequence (3' ITR), a transposase coding sequence and a promoter controlling the expression of the coding sequence of the transposase.

In certain embodiments, nucleic acid construct C disclosed herein comprises sequentially arranged: a transposon 5' inverted terminal repeat sequence (5' ITR), an EF1α promoter, a molecular brake (CD20) coding sequence, a CAR coding sequence, a coding sequence of anti-PD1 single-chain antibody, an immunoglobulin hinge region and an Fc coding sequence, a polyA tailing signal sequence, transposon 3' inverted terminal repeat sequence (3' ITR), a transposase coding sequence and a promoter (CMV) controlling the expression of the transposase coding sequence.

In certain embodiments, nucleic acid construct C disclosed herein comprises sequentially arranged: a transposon 5' inverted terminal repeat sequence (5' ITR), an EF1α promoter, a molecular brake (CD20) coding sequence, a CAR coding sequence, a coding sequence of anti-PD1 single-chain antibody, an IgG4 hinge region coding sequence, an IgG4 Fc coding sequence, a polyA tailing signal sequence, a transposon 3' inverted terminal repeat sequence (3' ITR), a transposase coding sequence and a promoter (CMV) controlling the expression of the transposase coding sequence.

In certain embodiments, nucleic acid construct C disclosed herein comprises sequentially arranged: a transposon 5' inverted terminal repeat sequence (5' ITR); a promoter controlling nucleic acid sequences encoding a molecular brake, a chimeric antigen receptor (CAR), a single-chain antibody of interest, an antibody hinge region and a transmembrane region; the nucleic acid sequences encoding the molecular brake, the chimeric antigen receptor (CAR), the agonistic single-chain antibody (such as the single-chain antibody of interest), the antibody hinge region and the transmembrane region directed by the agonistic antibody; a polyA tailing signal sequence; a transposon 3' inverted terminal repeat sequence (3' ITR); a transposase coding sequence; and a promoter controlling the expression of the transposase coding sequence.

In certain embodiments, nucleic acid construct C disclosed herein comprises sequentially arranged: a transposon 5' inverted terminal repeat sequence (5' ITR), an EF1α promoter, a molecular brake (CD20), a CAR, an anti-CD28 single-chain antibody, CD28 hinge region and transmembrane region, a polyA tailing signal sequence, a transposon 3' inverted terminal repeat sequence (3' ITR), a transposase coding sequence and a promoter (CMV) controlling the expression of the transposase coding sequence.

In some embodiments, nucleic acid construct A comprises a nucleic acid sequence as shown in SEQ ID NO: 3 or 7. In some embodiments, nucleic acid construct B comprises a nucleic acid sequence as shown in SEQ ID NO: 4. In some embodiments, nucleic acid construct C comprises a nucleic acid sequence as shown in SEQ ID NO: 11 or 14.

Nucleic acid constructs A, B and C disclosed herein can be recombinant expression vectors (recombinant expression vectors A, B and C), respectively, for expressing nucleic acid sequence(s) of interest and the nucleic acid sequence of the optional coding sequence for molecular brakes. Preferably, the expression vector is a transposon vector. In certain embodiments, the vector is one or more selected from the following transposon vectors: piggybac, sleeping beauty, frog prince, Tn5 and Ty. Besides the nucleic acid sequences comprised in nucleic acid constructs A, B and C, the expression vector generally comprises further elements which are usually included in the vector, such as multiple-cloning site(s), resistance gene(s), replication origin(s) and the like. It should be understood that in general, nucleic acid construct A/recombinant expression vector A of the invention does not comprise a coding sequence of transposase.

In certain embodiments, the recombinant expression vector uses pUC18, pUC19, pMD18-T, pMD19-T, pGM-T vector, pUC57, pMAX or pDC315 as its backbone. In other embodiments, the recombinant expression vector uses pCDNA3 series vectors, pCDNA4 series vectors, pCDNA5 series vectors, pCDNA6 series vectors, pRL series vectors, pUC57 vector, pMAX vector or pDC315 as its backbone. In certain embodiments, the present invention uses pSN vector constructed in CN201510638974.7, whose structure is as shown in FIG. 1 of thet application.

The present nucleic acid construct A/recombinant expression vector A and nucleic acid construct B/recombinant expression vector B, or nucleic acid construct C/recombinant expression vector C, can be transformed into cells of interest. The method for transformation is conventional method in the field, including but not limited to, virus transduction, microinjection, particle bombardment, gene gun transformation and electroporation and the like. In some embodiments, electroporation is employed to transfer the nucleic acid construct or recombinant expression vector.

The cells of interest can be various functional cells known in the art, for example, various killer cells, including but not limited to cytokine-induced killer cells (CIK), cytokine-induced killer cells stimulated by dendritic cells (DC-CIK), cytotoxic T lymphocytes (CTL), γδT cells, natural killer cells (NK), tumor infiltrating lymphocytes (TIL), lymphokine activated killer cells (LAK), CD3AK cells (anti-CD3 monoclonal antibody killer cells) and CAR-T/TCR-T cells. In some embodiments, the killer cells are T cells or NK cells.

Exemplary NK cells include, but are not limited to, primary NK cells, NK cell strains (such as NK92) and NKT cells. In some embodiments, the NK cells are primary NK cells. Exemplary T cells include, but are not limited to, peripheral blood T lymphocytes, cytotoxic T cells (CTLs), helper T cells, suppressing/regulating T cells, γδT cells and cytokine-induced killer cells (CIK), tumor infiltrating lymphocytes (TIL) and T cells in mixed cell populations thereof. In certain embodiments, the T cells are peripheral blood T lymphocytes and T cells derived from TIL.

Since nucleic acid construct A/recombinant expression vector A comprises ITR elements necessary for transposition but does not comprise a transposase, and nucleic acid construct B/recombinant expression vector B comprises an transposase necessary for the integration of exogenous genes, only in the cells transfected by both the nucleic acid construct A/recombinant expression vector A and the nucleic acid construct B/recombinant expression vector B can the integration of expression cassettes that comprise nucleic acid sequences of interest be realized. Furthermore, the nucleic acid sequence between transposon 5' ITR and transposon 3' ITR in nucleic acid construct A or recombinant expression vector A, together with 5' and 3' ITRs themselves are all integrated into the cell genome. When nucleic acid construct B/recombinant expression vector B comprises the nucleic acid sequence encoding the molecular brake, the cell will further express the molecular brake. Also, the nucleic acid sequence between transposon 5' ITR and transposon 3' ITR in nucleic acid construct B or the recombinant expression vector B, together with 5' and 3' ITRs themselves are all integrated into the cell genome.

On the other hand, when using nucleic acid construct C/recombinant expression vector C to transfect killer cells of interest, since it comprises ITR elements and transposase which are required for transposition, the nucleic acid sequence between transposon 5' ITR and transposon 3' ITR in the nucleic acid construct or the recombinant expression vector, together with the 5' and 3' ITRs themselves are all integrated into the cell genome of interest. When nucleic acid construct C/recombinant expression vector C comprises the nucleic acid sequence encoding a molecular brake, the cell will further express the molecular brake.

Therefore, the invention further provides a kind of killer cells, wherein the expression cassette comprising the nucleic acid sequence of interest is stably integrated in the genome of the killer cells. Furthermore, the sequentially linked transposon 5' inverted terminal repeat sequence (5'ITR), the promoter for controlling the expression of the nucleic acid sequence of interest, the nucleic acid sequence of interest, the polyA tailing signal sequence and transposon 3' inverted terminal repeat sequence (3'ITR), are stably integrated into the genome of the killer cell. In a preferred embodiment, the genome of the killer cells is further integrated with sequentially linked: the transposon 5' inverted terminal repeat sequence (5'ITR), the promoter for controlling the expression of the nucleic acid sequence of the molecular brake, the nucleic acid sequence encoding the molecular brake, the polyA tailing signal sequence and the transposon 3'inverted terminal repeat sequence (3'ITR).

In other embodiments, the genome of the killer cells is stably integrated with the expression cassette comprising the nucleic acid sequence encoding the CAR and the inhibitory antibody or agonistic antibody (such as a single-chain antibody of interest). Furthermore, the genome of the killer cells is stably integrated with transposon 5' inverted terminal repeat sequence (5'ITR); the promoter for controlling the expression of the nucleic acid sequences of a molecular brake, the chimeric antigen receptor (CAR) and the inhibitory antibody or agonistic antibody (such as a single-chain antibody of interest); the nucleic acid sequences encoding the molecular brake, the chimeric antigen receptor (CAR) and the inhibitory antibody or agonistic antibody (such as the single-chain antibody of interest); the polyA tailing signal sequence; and transposon 3'inverted terminal repeat sequence (3'ITR), linked in sequence.

In certain embodiments, the disclosure further provides a kind of transgenic NK cells, wherein the expression cassette comprising the nucleic acid sequence of interest is stably integrated in the genome of the transgenic NK cells. Furthermore, the sequentially linked transposon 5' inverted terminal repeat sequence (5' ITR), the promoter for controlling the expression of the nucleic acid sequence of interest, the nucleic acid sequence of interest, the polyA tailing signal sequence and transposon 3'inverted terminal repeat sequence (3' ITR), are stably integrated into the genome of the NK cell. In a preferred embodiment, the genome of the transgenic NK cells is further integrated with sequentially linked: transposon 5' inverted terminal repeat sequence (5'ITR), the promoter for controlling the expression of the nucleic acid sequence of the molecular brake, the nucleic acid sequence encoding the molecular brake, the polyA tailing signal sequence and transposon 3'inverted terminal repeat sequence (3' ITR).

In some embodiments, the transgenic NK cells herein stably express full-length sequences of antibody Fc segments or functional fragments thereof. In certain embodiments, the transgenic NK cells herein stably express antibody heavy chain constant region (such as Fc) and light chain. In certain embodiments, the transgenic NK cells herein stably express heavy chain(s) and light chain(s) of antibodies. In certain embodiments, nucleic acid construct A/recombinant expression vector A and nucleic acid construct B/recombinant expression vector B disclosed herein are transfected into the transgenic NK cells herein. In other embodiments, the amount of the antibody expressed per million of the transgenic NK cells disclosed herein within 48 hours is higher than 2 μg.

In certain embodiments, the invention further provides a kind of transgenic T cells, wherein the expression cassette comprising the nucleic acid sequence of interest is stably integrated in the genome of the transgenic T cells. Furthermore, the sequentially linked transposon 5' inverted terminal repeat sequence (5'ITR), the promoter for controlling the expression of the nucleic acid sequence of interest, the nucleic acid sequence of interest, the polyA tailing signal sequence and transposon 3'inverted terminal repeat sequence (3'ITR), are stably integrated into the genome of said T cell. In a preferred embodiment, the genome of the transgenic T cells is further integrated with transposon 5' inverted terminal repeat sequence (5'ITR), the promoter for controlling the expression of the nucleic acid sequence of the molecular brake, the nucleic acid sequence encoding the molecular brake, the polyA tailing signal sequence and transposon 3'inverted terminal repeat sequence (3'ITR), linked in sequence.

In some embodiments, the transgenic T cells herein stably express full-length sequences of antibody Fc segments or functional fragments thereof. In certain embodiments, the transgenic T cells herein stably express antibody heavy chain constant region (such as Fc) and light chain. In certain embodiments, the transgenic NK cells herein stably express heavy chain(s) and light chain(s) of antibodies. In certain embodiments, nucleic acid construct A/recombinant expression vector A and nucleic acid construct B/recombinant expression vector B disclosed herein are transfected into the transgenic T cells herein. In other embodiments, the amount of the antibody expressed per million of the transgenic T cells disclosed herein within 48 hours is higher than 2 μg.

In certain embodiments, the killer cells described herein are CAR-T cells, which express inhibitory antibodies. The antibody can be a secretory antibody or a membrane-anchoring antibody, preferably a secretory antibody. The antibody can be an immune checkpoint inhibitory antibody acting on T cell itself. Upon expression of said antibody in CAR-T cells, the cells are protected from being inhibited by tumor microenvironment, and residual tumor-specific T cells can be activated.

In other embodiments, the CAR-T cells express agonistic antibodies. The antibody can be a secretory antibody or a membrane-anchoring antibody, preferably a membrane-anchoring antibody. The antibody can be an immune co-stimulating molecule agonistic antibody acting on T cell itself. After the antibody is expressed by CAR-T cells, the clustering effect can be enhanced.

In some embodiments, the killer cells herein stably express full-length sequences of antibody Fc segments or functional fragments thereof, or stably express the antibody heavy chain constant region (such as Fc) or the full length sequence and the light chain full length sequence, or stably express CAR of interest and scFv of interest. In certain embodiments, nucleic acid construct A/recombinant expression vector A and nucleic acid construct B/recombinant expression vector B disclosed herein, or nucleic acid construct C/recombinant expression vector C disclosed herein are transfected into the killer cells herein. In other embodiments, the amount of the antibody expressed per million of killer cells within 48 hours is higher than 2 μg.

The killer cells disclosed herein have dual functions of cellular immunity and humoral immunity. Herein they are named pluripotent immune killer Cell (which is referred to as PIK for short), such as pluripotent immune killer T cell (PIK-T for short), and pluripotent natural killer cells (PIK-NK for short). On one hand, the cells can have anti-tumor cellular immunity (mainly mediated by killer cells). On the other hand, they have humoral immunity (mainly mediated by antibodies), which can effectively inhibit the proliferation of tumors, viruses and bacteria. Meanwhile, when the molecular brake exists, the killer cells herein can be removed by commercially available antibody medicines that recognize said molecular brake, which improves the safety of treatment.

According to the biological functions of the expressed antibodies, the killer cells disclosed herein can have different biological activities, including but not limited to, inhibiting tumors, viruses, bacteria and the like. Therefore, the killer cells disclosed herein can be used for inhibiting the growth of tumor cells, inhibiting the growth of viruses, treating tumors, treating viral infectious diseases, treating bacterial infectious diseases and treating autoimmune diseases. The tumors include, but are not limited to, liver cancer, lung cancer, colon cancer, pancreatic cancer, gastric cancer, breast cancer, nasopharyngeal carcinoma, lymphoma, ovarian cancer, bladder cancer, prostate cancer and head and neck tumors.

Therefore, also provided herein is a pharmaceutical composition, which comprises the killer cells described herein and a pharmaceutically acceptable carrier or excipient. Also provided herein is the use of the killer cells herein in the preparation of a medicament for inhibiting tumor cell growth, inhibiting virus growth, treating tumors, treating viral infectious diseases, treating bacterial infectious diseases and treating autoimmune diseases.

The invention also provides a method of transfecting killer cells (especially T cells and NK cells), the method comprising using two recombinant expression vectors to co-transfect the killer cells; wherein one recombinant expression vector comprises the expression cassette for the nucleic acid sequence of interest, and at both ends of the expression cassette, inverted terminal repeat sequences of the transposon are included; wherein the recombinant expression vector does not comprise a coding sequence of transposase; the other recombinant expression vector comprises the expression cassette of optional molecular brake(s), wherein at both ends of the expression cassette, the inverted terminal repeat sequences of the transposon are included, and the recombinant expression vector comprises a coding sequence of transposase. In one or more embodiments, the two recombinant expression vectors are the recombinant expression vectors A and B as described herein, respectively. Methods of transfection are well known in the art, including but not limited to one or more of virus transduction, micro-injection, particle bombardment, gene gun transformation and electroporation. During transfection, the usage amount of the two recombinant expression vectors can be adjusted according to specific situations. Usually, the amount ratio of the recombinant expression vector without transposase coding sequence to the recombinant expression vector with transposase coding sequence can be within the range of 1-5:1.

Therefore, the present invention further provides a kit comprising two kinds of recombinant expression vectors: one recombinant expression vector comprises the expression cassette for the nucleic acid sequence of interest, and at both ends of the expression cassette, inverted terminal repeat sequences of the transposon are included, wherein the recombinant expression vector does not comprise a coding sequence of transposase; the other recombinant expression vector comprises the expression cassette of optional molecular brake(s), and at both ends of the expression cassette, the inverted terminal repeat sequences of the transposon are included, wherein the recombinant expression vector comprises a coding sequence of transposase. In one or more embodiments, the two recombinant expression vectors are the recombinant expression vectors A and B as described herein, respectively. The kit can also comprises various reagents suitable for transfecting the recombinant expression vectors into cells, and optionally an instruction for guiding those skilled in the art to transfect the recombinant expression vectors into cells. In the kit, the two recombinant expression vectors can be independently packaged or can be packaged in the same container as a mixture.

Therefore, in certain embodiments, the present invention also relates to a composition of recombinant expression vectors, the composition comprising at least two recombinant expression vectors: one recombinant expression vector comprises the expression cassette for the nucleic acid sequence of interest, and at both ends of the expression cassette, inverted terminal repeat sequences of the transposon are included, wherein the recombinant expression vector does not comprise a coding sequence of transposase; the other recombinant expression vector comprises the expression cassette of optional molecular brake(s), and at both ends of the expression cassette, the inverted terminal repeat sequences of transposon are included, wherein the recombinant expression vector comprises a coding sequence of transposase. In one or more embodiments, the two recombinant expression vectors are the recombinant expression vectors A and B as described herein, respectively. The composition can comprise corresponding solvent(s) or carrier(s).

The present invention overcomes the deficiencies of the present commonly used gene transfection vector system (low transfection efficiency for killer cells, and low expression level of antibody), so that the immune killer cells can stably express high level of antibodies comprising full-length human Fc segment. The present invention overcomes the difficulty of insufficient cellular immune-therapy effect and the difficulty of macromolecular antibodies entering into solid tumors. In addition, the present killer cells can remain the cytotoxic while they can also stably express antibodies comprising human Fc segment at high levels, or stably express antibodies comprising human Fc segment, or stably express the antigen-binding fragment of the antibodies of interest and CAR. In addition, in order to prevent the proliferation of immune cells stably expressing antibodies in vivo which may lead to over-expression of the antibodies and in turn systemic toxicity and autoimmune disease, a molecular brake system (such as a CD20-Rituxan molecular brake system, CD20BR) is introduced. Using the commercially available monoclonal antibody (such as Rituxan), killing cells integrated with antibody expression cassette will be rapidly removed via the ADCC effect and CDC effect mediated by the monoclonal antibody, and thus the safety for therapy is effectively improved.

The embodiments of the present invention will be described in detail with reference to the examples. It will be understood by those skilled in the art that the following examples are only used for explaining the present invention, and should not be regarded as limiting the scope of the present invention. Where specific techniques or conditions are not detailed in the embodiments, they are carried out according to the techniques or conditions described in the literature of the field (see, for example, Molecular cloning. A laboratory manual by J Sambrook et al., and translated by Peitang HUANG et al., 3$^{rd}$ ed. Science Press, China) or carried out according to manufacturer's instruction. Reagent(s) or instrument(s) used herein, the manufacturers of which are not mentioned, are commercially available conventional products.

Example 1: Construction of Recombinant Plasmids pS838-AntiPD1 and pNB328-CD20BR

Two DNA sequences as shown below were synthesized by Shanghai Genray Biotech Co., Ltd:

```
Seq1:
                            (SEQ ID NO: 1)
CGATAGGACGCTGATCTTAAT

Seq2:
                            (SEQ ID NO: 2)
TACCTGCGACTAGAAT
```

The DNA sequences were denatured at 98° C. for 5 minutes, and allowed to cool down naturally to form a double-stranded DNA linker with ClaI and PacI cohesive ends at the upstream and downstream sides, respectively.

pNB vector was double digested by CaII and PacI (constructed according to CN201510638974.7) and loaded with the above mentioned double-stranded DNA to obtain pS vector.

CCEF promoter sequence (disclosed in CN201510021408.1) was synthesized by Shanghai Genray Biotech Co., Ltd, with XbaI and EcoRI restriction sites introduced into its upstream and downstream, respectively. The promoter was loaded into pS vector which was double digested by XbaI and EcoRI, so as to obtain pS838 vector.

PD1 antibody coding sequence as shown in SEQ ID NO: 3 was synthesized by Shanghai Genray Biotech Co., Ltd, with EcoRI and SaiI restriction sites introduced into its upstream and downstream, respectively, and loaded into pS838 vector to obtain pS838-AntiPD1.

```
antiPD1 coding sequence:
                            (SEQ ID NO: 3)
GAATTCGCCACCATGGAAGCCCCAGCTCAGCTTCTCTTCCTCCTGCTACTC

TGGCTCCCAGATACCACCGGACAGGTGTACTTGGTAGAGTCTGGGGGAGGC

GTGGTCCAGCCTGGGAGGTCCCTGAGACTCTCCTGTGCAGCGTCTGGATTC

ACCTTCAGTAACTATGGCATGCACTGGGTCCGCCAGGCTCCAGGCAAGGGG

CTGGAGTGGGTGGCACTTATATGGTATGATGGAAGTAATAAATACTATGCA

GACTCCGTGAAGGGCCGATTCACCATCTCCAGAGACAATTCCAAGAACACG

CTGTATCTGCAAATGACCAGTCTGAGAGTCGAGGACACGGCTGTGTATTAT

TGTGCGAGCAACGTTGACCATTGGGGCCAGGGAACCCTGGTCACCGTCTCC

TCAGCTTCCACCAAGGGCCCATCCGTCTTCCCCCTGGCGCCCTGCTCCAGG

AGCACCTCCGAGAGCACAGCCGCCCTGGGCTGCCTGGTCAAGGACTACTTC

CCCGAACCGGTGACGGTGTCGTGGAACTCAGGCGCCCTGACCAGCGGCGTG

CACACCTTCCCGGCTGTCCTACAGTCCTCAGGACTCTACTCCCTCAGCAGC

GTGGTGACCGTGCCCTCCAGCAGCTTGGGCACGAAGACCTACACCTGCAAC

GTAGATCACAAGCCCAGCAACACCAAGGTGGACAAGAGAGTTGAGTCCAAA

TATGGTCCCCCATGCCCACCATGCCCAGCACCTGAGTTCCTGGGGGGACCA

TCAGTCTTCCTGTTCCCCCCAAAACCCAAGGACACTCTCATGATCTCCCGG

ACCCCTGAGGTCACGTGCGTGGTGGTGGACGTGAGCCAGGAAGACCCCGAG

GTCCAGTTCAACTGGTACGTGGATGGCGTGGAGGTGCATAATGCCAAGACA

AAGCCGCGGGAGGAGCAGTTCAACAGCACGTACCGTGTGGTCAGCGTCCTC

ACCGTCCTGCACCAGGACTGGCTGAACGGCAAGGAGTACAAGTGCAAGGTC

TCCAACAAAGGCCTCCCGTCCTCCATCGAGAAAACCATCTCCAAAGCCAAA

GGGCAGCCCCGAGAGCCACAGGTGTACACCCTGCCCCCATCCCAGGAGGAG

ATGACCAAGAACCAGGTCAGCCTGACCTGCCTGGTCAAAGGCTTCTACCCC

AGCGACATCGCCGTGGAGTGGGAGAGCAATGGGCAGCCGGAGAACAACTAC

AAGACCACGCCTCCCGTGCTGGACTCCGACGGCTCCTTCTTCCTCTACAGC

AGGCTAACCGTGGACAAGAGCAGGTGGCAGGAGGGGAATGTCTTCTCATGC

TCCGTGATGCATGAGGCTCTGCACAACCACTACACACAGAAGAGCCTCTCC

CTGTCTCTGGGTAAACGTAAAAGGCGAGCTCCTGTTAAACAGACTTTGAAT

TTTGACCTTCTCAAGTTGGCGGGAGACGTCGAGTCCAACCCTGGGCCCATG

GAAGCCCCAGCTCAGCTTCTCTTCCTCCTGCTACTCTGGCTCCCAGATACC

ACCGGAGAAATTGTGTTGACACAGTCTCCAGCCACCCTGTCTTTGTCTCCA

GGGGAAAGAGCCACCCTCTCCTGCAGGGCCAGTCAGAGTGTTAGTAGTTAC

TTAGCCTGGTACCAACAGAAACCTGGCCAGGCTCCCAGGCTCCTCATCTAT

GATGCATCCAACAGGGCCACTGGCATCCCAGCCAGGTTCAGTGGCAGTGGG
```

-continued

```
TCTGGGACAGACTTCACTCTCACCATCAGCAGCCTAGAGCCTGAAGATTTT

GCAGTTTATTACTGTCAGCAGAGTAGCAACTGGCCTCGGACGTTCGGCCAA

GGGACCAAGGTGGAAATCAAACGAACTGTGGCTGCACCATCTGTCTTCATC

TTCCCGCCATCTGATGAGCAGTTGAAATCTGGAACTGCCTCTGTTGTGTGC

CTGCTGAATAACTTCTATCCCAGAGAGGCCAAAGTACAGTGGAAGGTGGAT

AACGCCCTCCAATCGGGTAACTCCCAGGAGAGTGTCACAGAGCAGGACAGC

AAGGACAGCACCTACAGCCTCAGCAGCACCCTGACGCTGAGCAAAGCAGAC

TACGAGAAACACAAAGTCTACGCCTGCGAAGTCACCCATCAGGGCCTGAGC

TCGCCCGTCACAAAGAGCTTCAACAGGGGAGAGTGTTGATAAGTCGAC,
``` wherein double underline represents restriction sites, and single underline represents Furin 2A coding sequence.

CD20BR coding sequence as shown in SEQ ID NO: 4 was synthesized by Shanghai Genray Biotech Co., Ltd, with EcoRI and SalI restriction sites introduced into its upstream and downstream respectively, and loaded into pNB328 vector (constructed according to CN201510638974.7) and named as pNB328-CD20BR.

CD20BR coding sequence:
(SEQ ID NO: 4)
```
GAATTCGCCACCATGGAGTTTTGGCTGAGCTGGGTTTTCCTTGTTGCTATT

TTAAAAGGTGTCCAGTGTAACATATACAACTGTGAACCAGCTAATCCCTCT

GAGAAAAACTCCCCATCTACCCAATACTGTTACAGCATACAATCTCTGGGT

GGAGGTGGAGGTGGAGGTGGAGGTATCTACATCTGGGCGCCCTTGGCCGGG

ACTTGTGGGGTCCTTCTCCTGTCACTGGTTATCACCCTTTACTGCAACCAC

AGGAACCGTAAAAGGCGAGCTCCTGTTAAACAGACTTTGAATTTTGACCTT

CTCAAGTTGGCGGGAGACGTCGAGTCCAACCCTGGGCCCATGGTGAGCAAG

CAGATCCTGAAGAACACCGGCCTGCAGGAGATCATGAGCTTCAAGGTGAAC

CTGGAGGGCGTGGTGAACAACCACGTGTTCACCATGGAGGGCTGCGGCAAG

GGCAACATCCTGTTCGGCAACCAGCTGGTGCAGATCCGCGTGACCAAGGGC

GCCCCCCTGCCCTTCGCCTTCGACATCCTGAGCCCCGCCTTCCAGTACGGC

AACCGCACCTTCACCAAGTACCCCGAGGACATCAGCGACTTCTTCATCCAG

AGCTTCCCCGCCGGCTTCGTGTACGAGCGCACCCTGCGCTACGAGGACGGC

GGCCTGGTGGAGATCCGCAGCGACATCAACCTGATCGAGGAGATGTTCGTG

TACCGCGTGGAGTACAAGGGCCGCAACTTCCCCAACGACGGCCCCGTGATG

AAGAAGACCATCACCGGCCTGCAGCCCAGCTTCGAGGTGGTGTACATGAAC

GACGGCGTGCTGGTGGGCCAGGTGATCCTGGTGTACCGCCTGAACAGCGGC

AAGTTCTACAGCTGCCACATGCGCACCCTGATGAAGAGCAAGGGCGTGGTG

AAGGACTTCCCCGAGTACCACTTCATCCAGCACCGCCTGGAGAAGACCTAC

GTGGAGGACGGCGGCTTCGTGGAGCAGCACGAGACCGCCATCGCCCAGCTG

ACCAGCCTGGGCAAGCCCCTGGGCAGCCTGCACGAGTGGGTGTGAGTCGAC
b,
``` wherein double underline represents restriction sites, and single underline represents CD20 epitope recognized by Rituxan antibody.

The schematic diagrams of pNB328-CD20BR and pS838-antiPD1 vectors are shown in FIG. 1.

Example 2: Genetic Modification of Peripheral Blood T Lymphocytes $1 \times 10^7$ freshly isolated peripheral blood mononuclear cell (PBMC) were prepared, pNB328-CD20BR and pS838-antiPD1 were co-transfected at the ratio of 1:2 into cell nucleus by Lonza 2b-Nucleofector. The cells were incubated at 37° C., 5% $CO_2$ in an incubator: after 6 hours, cells were transferred to a 6-well plate containing 30 ng/ml anti-CD3 antibody and 3000 IU/ml IL-2 (purchased from Novoprotein), and incubated at 37° C., 5% $CO_2$ in an incubator. After the cells had reached the state of healthy growth, cells were obtained as pluripotent T cells expressing PD-1, abbreviated as PIK-T. Non-transfected PBMCs were plated on culture plates containing 30 ng/ml anti-CD3 antibody and 3000 IU/ml IL-2 (purchased from Novoprotein), and incubated at 37° C. 5% $CO_2$ as control. Since only pNB328 vector contains transposase necessary for the integration of the exogenous genes while pS838 only contains ITR elements necessary for transposition, only cells co-transfected with both pNB328-CD20BR and pS838-antiPD1 vectors can realize the integration of PD1 antibody expression cassette, thus ensuring that all the PIK-T cells have CD20 molecular brakes.

Example 3: Quantitative Assay of the Amount of PD1 Antibody Expression in PIK-T Cells PIK-T and control T cells obtained in Example 2 were passaged at a split ratio of 1:3. After two weeks, they were plated in 6-well plates supplemented with 4 ml AIM-V solution (purchased from GIBCO) at the density of $1.0 \times 10^6$ cells/well and incubated at 37° C., 5% $CO_2$ in an incubator. After incubating for 24 hours, 48 hours, 72 hours and 96 hours, 800 µl of supernatant was collected and stored for later use at −20° C. ELISA plates (purchased from Sino-Biological) were coated with humanized PD1 recombinant protein, and HRP-labeled mouse anti-human IgG mAb (purchased from Abcam) was used for the assay, with commercialized anti-PD1 antibody (purchased from Merck) as reference standard. The amount of PD1 antibody expression was measured by double-sandwich ELISA.

Figure 2A:
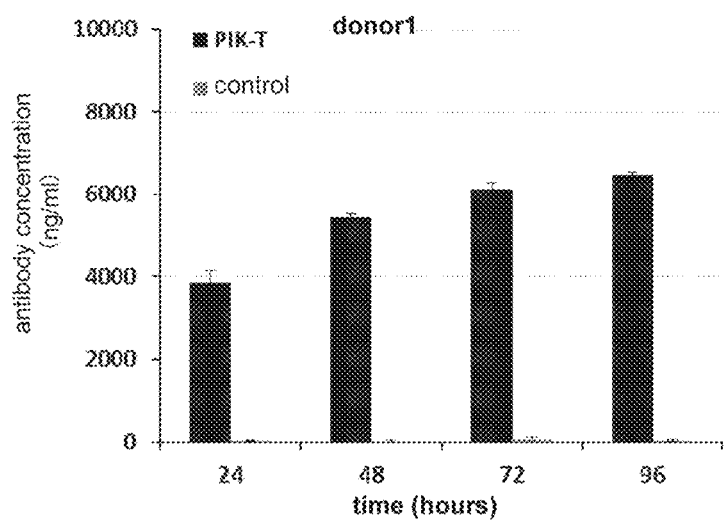
FIGS. 2A, 2B and 2C: ELISA assays of PD1 antibody expression levels in PIK-T cells from different donors. The control is non-transgenic T cells of the same origin.
Figure 2B:
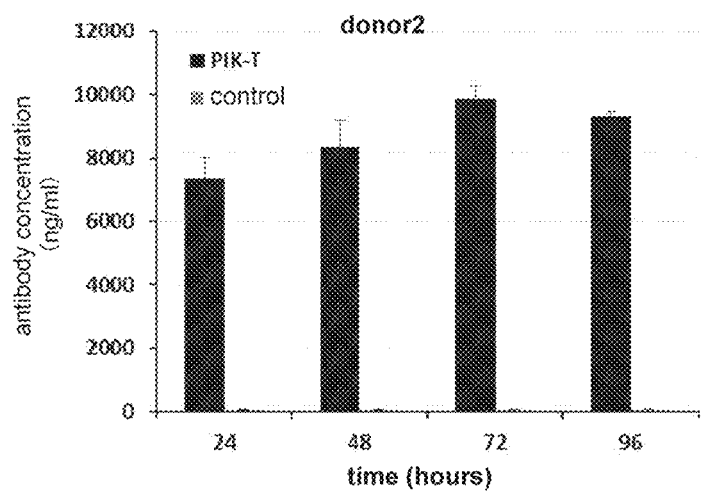
Figure 2C:
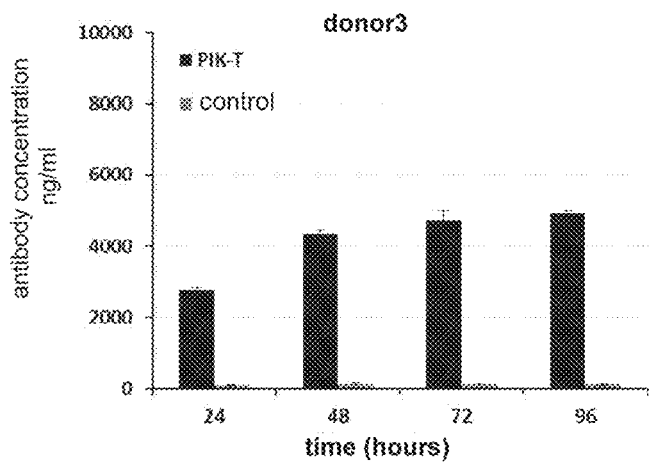

Results show that PIK-T cells from 3 different donors can all stably express high level of PD1 antibody, as shown in FIGS. 2A, 2B and 2C.

Example 4: Qualitative Assay of the Expression of PD1 Antibody in PIK-T Cells

Figure 3:
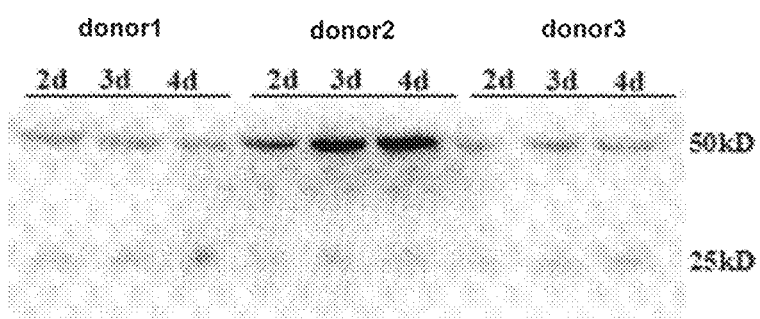
FIG. 3: Western blotting assay of the expression of PD1 antibody in PIK-T cells from different donors.

PIK-T cells obtained in Example 2 were plated in 6-well plates supplemented with 4 ml AIM-V solution at the density of $1.0 \times 10^6$ cells/well and incubated at 37° C. 5% $CO_2$ in an incubator. After incubating for 48 hours, 72 hours and 96 hours, supernatant harboring cells was collected. To 120 µl supernatant collected at each time point was added 30 µl of 5×SDS-PAGE Loading buffer, and the sample was boiled at 100° C. for 10 minutes, and stored for later use at −20° C. Western blotting assay for the detection of the anti-PD1 antibody expression was carried out using goat anti-human IgG (H+L) as the primary antibody and HRP-rabbit-anti-goat antibody as the secondary antibody, both purchased from Jackson ImmunoResearch. Results show that anti-PD1 antibody expressed by PIK cells comprises the correct heavy chains (50 kD) and light chain (25 kD), as shown in FIG. 3.

Example 5: Detection of PD1 Antibody Expression Cassette in PIK-T Cell Genome

Figure 4:
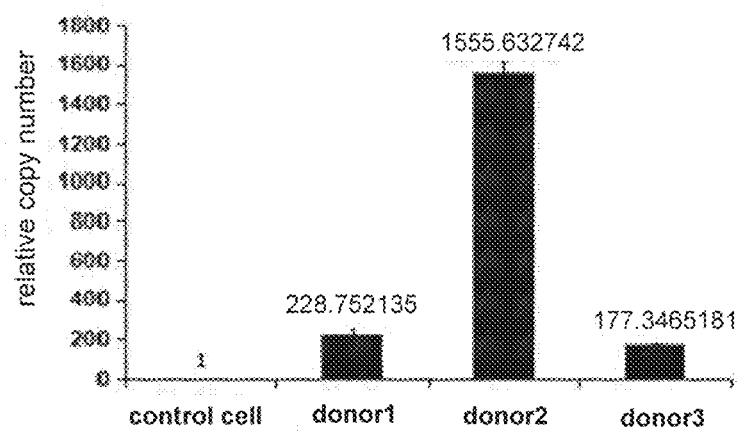
FIG. 4: The detection of PD1 antibody expression cassette in PIK-T cell genome.

Genomic DNA from PIK-T cells obtained in Example 2 and control T cells were extracted according to the instruction included in the kit. DNA concentrations of the PIK-T cells and the control T cells were measured by fluorescent real-time quantitative PCR with the following reaction program: 95° C., 15 s→95° C., 5 s→60° C., 15 s, 40 cycles. Results show that PD1 antibody expression cassette is integrated into T cell genome, as shown in FIG. 4.
Primer Sequences:
F: ATCTCCAAAGCCAAAGGGCA (SEQ ID NO: 5);
R: CGATGTCGCTGGGGTAGAAG (SEQ ID NO: 6).

Example 6: Flow Cytometric Detection of PD1 Molecules on PIK-T Cell Surface

Figure 5:
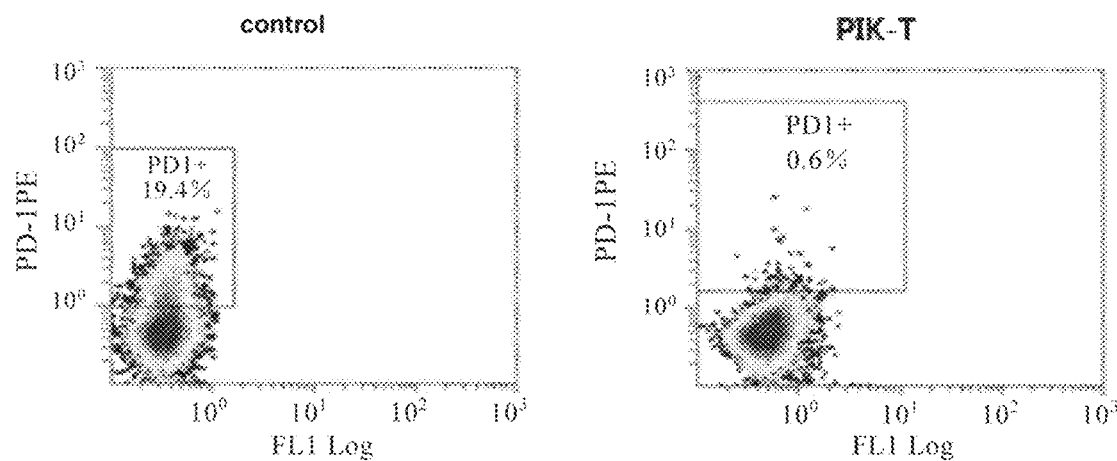
FIG. 5: Flow cytometry assay of PD1 molecules on the surface of PIK-T cells.

Suspended PIK-T cells (obtained in example 2) and control T cells were collected and counted, then added into two 1.5 ml EP tubes respectively at $1\times10^6$ cells/tube, washed twice with PBS and centrifuged at 1,200 rpm for 5 minutes. Supernatants were discarded, 2 µl of isotype control antibody IgG1-PE and anti-CD279-PE antibodies (both purchased from BD) were added respectively. Pellets were tapped gently until well mixed, incubated for 30 minutes at room temperature in the dark, washed with PBS once, and centrifuged at 1,200 rpm for 5 minutes. Supernatants were discarded, 400 µl of normal saline was added before transferring the cells into flow cytometry tubes, and the sample was loaded onto the flow cytometry device for detection. Experimental results show that compared to control cells, PIK-T cells have significantly reduced number of PD1 molecules, indicating that PIK-T cells can effectively block cell surface PD1 molecules by secreting PD1 antibody through autocrine and paracrine, as shown in FIG. 5.

Example 7: Proliferation Assay of PIK-T Cells

Figure 6:
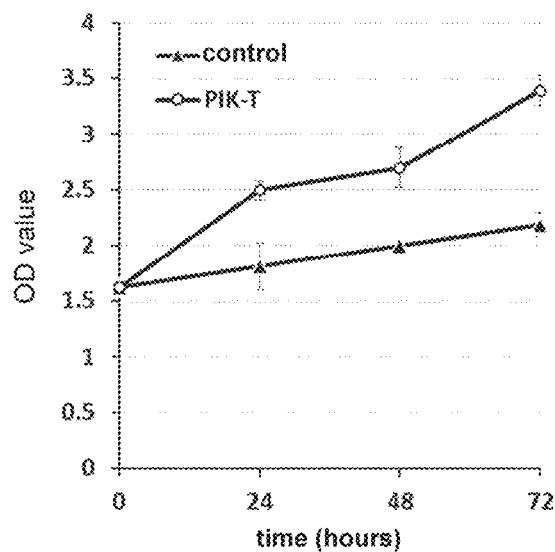
FIG. 6: PIK-T cell proliferation assay.

PIK-T cells obtained in Example 2 and control T cells were plated in 96-well plates at the density of $4\times10^4$ cells/well (each cell type in triplicate, with a total volume of 200 µl), and incubated at 37° C., 5% $CO_2$ in an incubator. After the cells were incubated for 24 hours, 48 hours, 72 hours and 96 hours, 20 µl of of CCK8 reagent was added before the samples were incubated for 6 hours at 37° C. in the dark. The $OD_{450}$ value was measured on ELISA analyzer, and cell number was calculated based on standard curve. Results show that the proliferation speed of PIK-T cells is significantly higher than that of control T cells, indicating that antibody secreted by PIK-T cells can promote the proliferation of T cells, as shown in FIG. 6.

Figure 7:
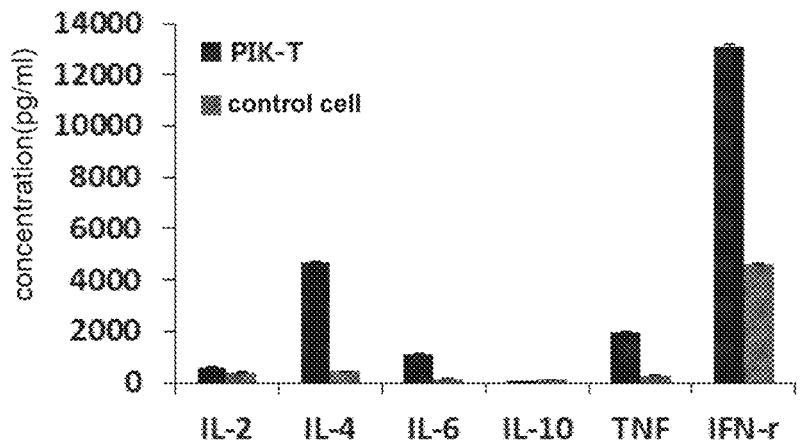
FIG. 7: Assay of PIK-T cell secretion of cytokines IL-2, IL-4, IL-6, IL-10, TNFα and IFN-γ.

Example 8: Cytokine Secretion Assay of PIK-T Cells 24-well plate was coated by 5 µg/ml CD3 antibody (purchased from Novoprotein) overnight at 4° C., washed with PBS three times, and $3\times10^5$ PIK-T cells obtained in Example 2 and control T cells were added to the plate and incubated for 24 h before collecting the cell-containing supernatant. Cytokine secretion of PIK-T cells and control T cells after CD3 antibody stimulation was determined by BD™ CBA Human Th1/Th2 Cytokine Kit II (purchased from BD). Results show that IL-4, IL-6, TNF-α and IFN-γ secreted by PIK-T cells are remarkably enhanced compared to control T cells, while the secretion of the two cytokines, IL-2 and IL-10, do not have significant difference, as shown in FIG. 7.

Example 9: In Vitro Tumor Cell Killing Assay of TIL-Derived PIK-T Cells

Freshly-removed lung cancer specimens were collected and immediately processed under aseptic conditions. The specific method comprises the following steps: normal tissue and necrotic areas around lung cancer specimens were removed, and small pieces of tissues sized 1-2 mm³ from different areas of the specimen were collected and added into a 24-well plate at one piece/well. To each well, 2 mL of Complete Culture medium (GT-T551 culture medium with 10% FBS) and 3000 IU/ml IL-2 were added, and then the plate was incubated in an incubator at 37° C. and 5% $CO_2$. After 5-6 days from the start of the incubation, half of the medium for all the wells was replaced with fresh medium. After that, according to the growth condition of tumor infiltrating lymphocyte (TIL), half of the medium was replaced every 1-2 days. Once TILs in the wells reached confluency and all the adherent cells had been removed, the TILs that had filled each well were collected. Then, $1\times10^6$ TILs were re-suspended in a T175 culture flasks with 150 ml of complete culture medium, 30 ng/ml anti-CD3 antibody, radiated feeder cells (PBMCs from three different healthy people) no less than 200 times of the TILs and 6000 IU/ml IL-2, and the bottle was vertically cultured. On Day 5 of culture, 65% of the liquid in the bottle was replaced with fresh complete culture medium with IL-2. On Day 7 of culture, cell suspension in the two T175 culture flasks were transferred into cell culture bag, and 300 mL of complete culture medium with IL-2 were added. From Day 6 on, Trypan blue staining and cell counting were carried out every other day and cell density was kept at $0.5\text{-}2\times10^6$/mL by adding fresh complete culture medium with IL-2. Then, following the method of Example 2, pNB328-CD20BR and pS838-antiPD1 plasmids were transfected to obtain TIL-derived PIK-T cells.

Figure 8:
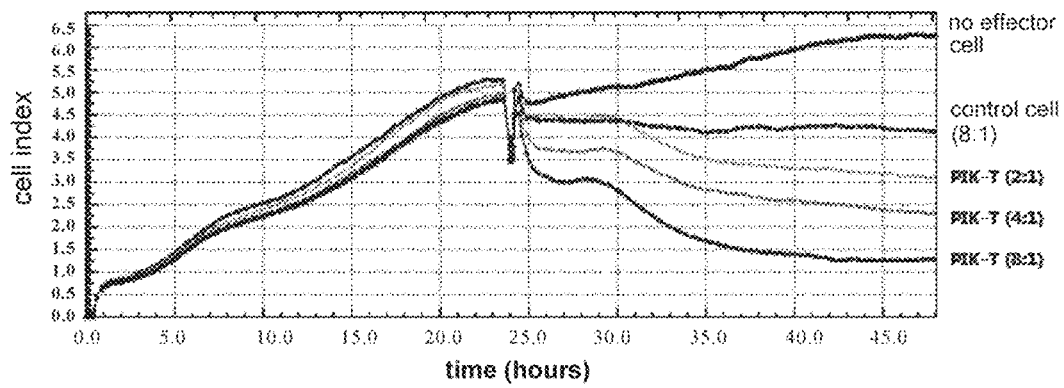
FIG. 8: The detection of in vitro cytotoxity of PIK-T cells on tumor cells.

Lung cancer cell strain NCI-H460 (purchased from American typical culture center. ATCC) with matched MHC class I type was chosen and plated on RTCA cell proliferation plate (purchased from ACEA Biosciences. USA) at a ratio of 10,000 cells/well. Then, according to the manufacturer's instruction, the in vitro killing activity of the cells was detected on real-time unlabeled cell function analyzer (RTCA), with the effector:target ratios being 8:1, 4:1, and 2:1, respectively. TILs not transfected with plasmids were used as control (E:T=8:1), and cell proliferation curve was observed. Results show that compared to control cells, PIK-T cell can kill H446 tumor cells more efficiently, as shown in FIG. 8.

Figure 9:
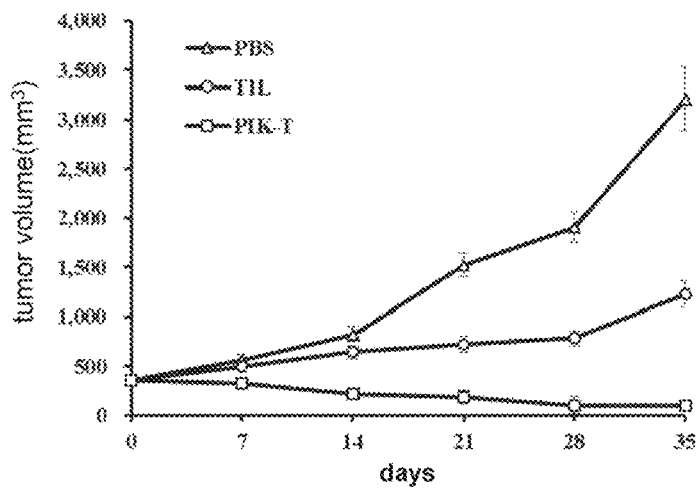
FIG. 9: The detection of in vivo inhibitory effects of PIK-T cells on the transplanted tumor.

Example 10: In Vivo Assay for Treating Tumor Xenograft with TIL-Derived PIK-T Cells NOD-SCID mice (purchased from Shanghai SLAC Laboratory Animal Co., Ltd) were subcutaneously injected with $5\times10^6$ H446 malignant lung cancer cells. After 10 days, TIL-derived PIK-T cells (prepared in Example 9), control TIL cells (injection dosage $2\times10^5$) or PBS buffer were administered via tail vein injection, respectively. The growth condition of the tumor xenograft was measured. Results show a significant difference between the inhibitory effects of PIK-T cells on lung cancer and that of the control group (FIG. 9).

Example 11: In Vivo Clearance Assay of PIK-T Cells (Validation of Molecular Brake Function)

BABL/c nude mice (purchased from Shanghai SLAC Laboratory Animal Co., Ltd) were injected with PIK-T cells prepared in Example 2 via tail vein (injection dosage 5×10$^6$). After 3 days, 100 μg of Rituxan antibody or human IgG control antibody were injected intravenously. After 12 hours, blood and bone marrow samples were collected, and flow cytometer was used for detecting the proportion of PIK-T cells (CD20 and CD3 dual-positive cells).

Figure 10:
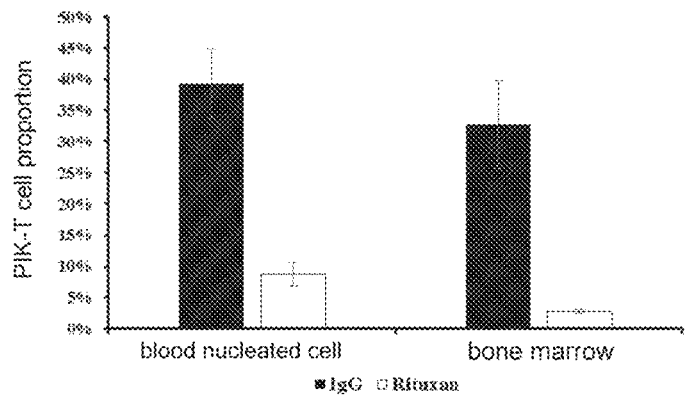
FIG. 10: Functional detection of the molecular brake system in PIK-T cells.

Results show that compared to control group injected with human IgG antibody, after injection of Rituxan antibody, the proportions of the infused PIK-T cells in blood and bone marrow were remarkably reduced (FIG. 10). Therefore, CD20 molecular brake can effectively act in vivo and remove PIK-T cells with CD20 epitope by ADCC and CDC effects.

Example 12: Construction of Recombinant Plasmid pS838-AntiHER2 pS38-AntiHER2 recombinant plasmid was constructed according to a method similar to Example 1.
Specifically, HER2 antibody coding sequence as shown in SEQ ID NO: 7 was synthesized by Shanghai Genray Biotech Co., Ltd, with EcoRI and SalI restriction sites introduced into its upstream and downstream, respectively, loaded into pS838 vector, and named pS838-AntiHER2.

antiHER2 coding sequence:
(SEQ ID NO: 7)
GAATTCGCCACCATGGAGTTTTGGCTGAGCTGGGTTTTCCTTGTTGCTATT

TTAAAAGGTGTCCAGTGTGAGGTTCAGCTGGTGGAGTCTGGCGGTGGCCTG

GTGCAGCCAGGGGGCTCACTCCGTTTGTCCTGTGCAGCTTCTGGCTTCAAC

ATTAAAGACACCTATATACACTGGGTGCGTCAGGCCCCGGGTAAGGGCCTG

GAATGGGTTGCAAGGATTTATCCTACGAATGGTTATACTAGATATGCCGAT

AGCGTCAAGGGCCGTTTCACTATAAGCGCAGACACATCCAAAAACACAGCC

TACCTGCAGATGAACAGCCTGCGTGCTGAGGACACTGCCGTCTATTATTGT

TCTAGATGGGGAGGGGACGGCTTCTATGCTATGGACTACTGGGGTCAAGGA

ACCCTGGTCACCGTCTCCTCGGCCTCCACCAAGGGCCCATCGGTCTTCCCC

CTGGCACCCTCCTCCAAGAGCACCTCTGGGGGCACAGCGGCCCTGGGCTGC

CTGGTCAAGGACTACTTCCCCGAACCGGTGACGGTGTCGTGGAACTCAGGC

GCCCTGACCAGCGGCGTGCACACCTTCCCGGCTGTCCTACAGTCCTCAGGA

CTCTACTCCCTCAGCAGCGTGGTGACCGTGCCCTCCAGCAGCTTGGGCACC

CAGACCTACATCTGCAACGTGAATCACAAGCCCAGCAACACCAAGGTGGAC

AAGAAAGTTGAGCCCAAATCTTGTGACAAAACTCACACATGCCCACCGTGC

CCAGCACCTGAACTCCTGGGGGGACCGTCAGTCTTCCTCTTCCCCCCAAAA

CCCAAGGACACCCTCATGATCTCCCGGACCCCTGAGGTCACATGCGTGGTG

GTGGACGTGAGCCACGAAGACCCTGAGGTCAAGTTCAACTGGTACGTGGAC

GGCGTGGAGGTGCATAATGCCAAGACAAAGCCGCGGGAGGAGCAGTACAAC

-continued
AGCACGTACCGTGTGGTCAGCGTCCTCACCGTCCTGCACCAGGACTGGCTG

AATGGCAAGGAGTACAAGTGCAAGGTCTCCAACAAAGCCCTCCCAGCCCCC

ATCGAGAAAACCATCTCCAAAGCCAAAGGGCAGCCCCGAGAACCACAGGTG

TACACCCTGCCCCCATCCCGGGATGAGCTGACCAAGAACCAGGTCAGCCTG

ACCTGCCTGGTCAAAGGCTTCTATCCCAGCGACATCGCCGTGGAGTGGGAG

AGCAATGGGCAGCCGGAGAACAACTACAAGACCACGCCTCCCGTGCTGGAC

TCCGACGGCTCCTTCTTCCTCTACAGCAAGCTCACCGTGGACAAGAGCAGG

TGGCAGCAGGGGAACGTCTTCTCATGCTCCGTGATGCATGAGGCTCTGCAC

AACCACTACACGCAGAAGAGCCTCTCCCTGTCTCCGGGTAAACGTAAAAGG

CGAGCTCCTGTTAAACAGACTTTGAATTTTGACCTTCTCAAGTTGGCGGGA

GACGTCGAGTCCAACCCTGGGCCCATGGAAGCCCCAGCTCAGCTTCTCTTC

CTCCTGCTACTCTGGCTCCCAGATACCACCGGAGATATCCAGATGACCCAG

TCCCCGAGCTCCCTGTCCGCCTCTGTGGGCGATAGGGTCACCATCACCTGC

CGTGCCAGTCAGGATGTGAATACTGCTGTAGCCTGGTATCAACAGAAACCA

GGAAAAGCTCCGAAACTACTGATTTACTCGGCATCCTTCCTCTACTCTGGA

GTCCCTTCTCGCTTCTCTGGATCCAGATCTGGGACGGATTTCACTCTGACC

ATCAGCAGTCTGCAGCCGGAAGACTTCGCAACTTATTACTGTCAGCAACAT

TATACTACTCCTCCCACGTTCGGACAGGGTACCAAGGTGGAGATCAAAACT

GTGGCTGCACCATCTGTCTTCATCTTCCCGCCATCTGATGAGCAGTTGAAA

TCTGGAACTGCCTCTGTTGTGTGCCTGCTGAATAACTTCTATCCCAGAGAG

GCCAAAGTACAGTGGAAGGTGGATAACGCCCTCCAATCGGGTAACTCCCAG

GAGAGTGTCACAGAGCAGGACAGCAAGGACAGCACCTACAGCCTCAGCAGC

ACCCTGACGCTGAGCAAAGCAGACTACGAGAAACACAAAGTCTACGCCTGC

GAAGTCACCCATCAGGGCCTGAGCTCGCCCGTCACAAAGAGCTTCAACAGG

GGAGAGTGTTGATAAGTCGAC, wherein double underline represents restriction sites, and single underline represents Furin 2A coding sequence.

Figure 11:
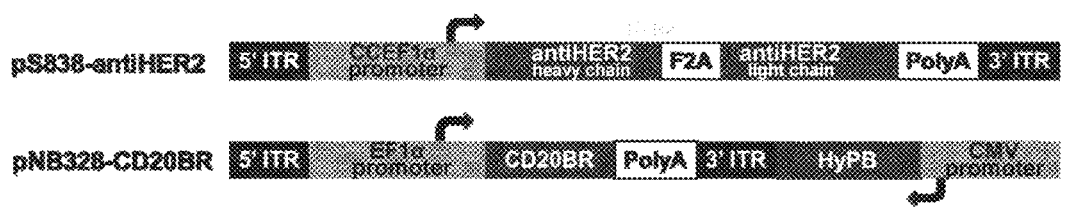
FIG. 11: A schematic diagram of the expression cassette of HER2 antibody. ITR is a transposon's inverted terminal repeat sequence; HyPB is a piggybac transposase.

The schematic diagrams of pNB328-CD20BR (constructed as described in Example 1) and pS838-antiHER2 vectors are shown in FIG. 11.

Example 13: Genetic Modification of Peripheral Blood-Derived NK Cells

Freshly isolated peripheral blood mononuclear cells (PBMC) were prepared, added into culture plate (purchased from STEMCELL Technologies) containing 30 ng/ml anti-CD16 antibody, 500 IU/ml IL-21 (purchased from Novoprotein) and 3 ml of NK medium, and incubated at 37° C. 5% $CO_2$ in an incubator, 5×10$^6$ NK cells were collected, and pNB328-CD20BR and pS838-antiHER2 were co-transfected at a ratio of 1:2 into cell nucleus by Lonza 2b-Nucleofector. After the cells had reached the state of healthy growth, pluripotent NK cells expressing HER2 antibody were obtained, abbreviated as PIK-NK. Since only pNB328 vector contains the transposase necessary for the integration of the exogenous genes while pS838 vector only contains the ITR elements necessary for transposition, only in the cells co-transfected with pNB328-CD20BR and pS838-antiHER2 vectors can the integration of HER2 antibody expression cassette be realized, thus ensuring that all PIK-NK cells have CD20 molecular brakes.

Example 14: Quantitative Assay of the Amount of Anti-HER2 Antibody Expression in PIK-NK Cells PIK-NK cells obtained in Example 13 and control T cells were passaged at a split ratio of 1:3, and plated in 6-well plates supplemented with NK culture solution (purchased from STEMCELL Technologies) at the density of $1.0 \times 10^6$ cells/well and incubated at 37° C., 5% $CO_2$ in an incubator. After incubating for 24 hours, 48 hours, 72 hours and 96 hours, 800 µl of cell-containing supernatant was collected and stored at −20° C. for later use. ELISA plates (purchased from SinoBiological) were coated with human recombinant HER2 protein, and HRP-labeled mouse anti-human IgG mAb (purchased from Abcam) was used for the assay, with commercialized anti-HER2 antibody (Herceptin, purchased from Roche) as reference standard. The amount of HER2 antibody expression was measured by double-sandwich ELISA.

Figure 12A:
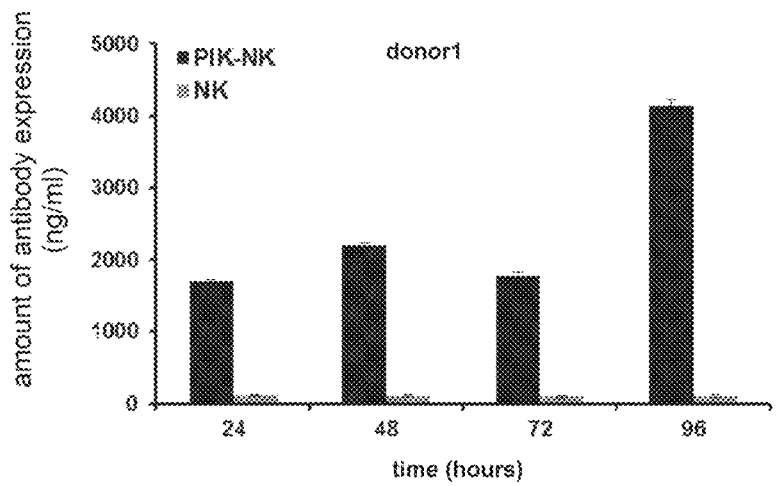
FIGS. 12A and 12B: ELISA assays of HER2 antibody expression levels in PIK-NK cells from different donors. The control is non-transgenic NK cells of the same origin.
Figure 12B:
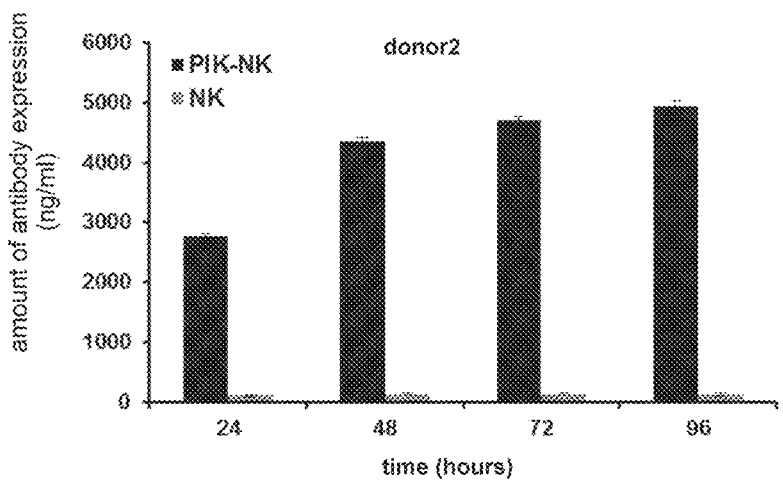

Results show that PIK-NK cells from 2 different donors can both stably express anti-HER2 antibody at high level, as shown in FIGS. 12A and 12B.

Figure 13:
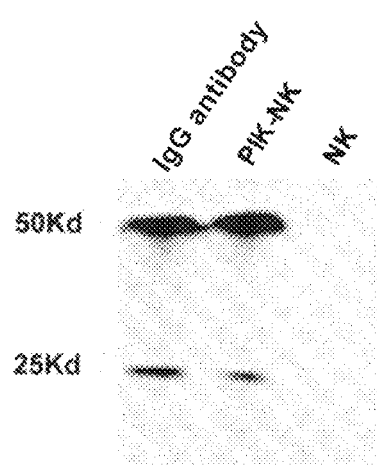
FIG. 13: Western blotting assay of the expression of HER2 antibody in PIK-NK.

Example 15: Qualitative Assay of the Expression of Anti-HER2 Antibody in PIK-NK Cells PIK-NK cells obtained in Example 13 were plated in 6-well plates supplemented with 4 ml of NK culture solution (purchased from STEMCELL Technologies) at the density of $1.0 \times 10^6$ cells/well and incubated at 37° C., 5% $CO_2$ in an incubator. After incubating for 48 hours, cell-containing supernatant was collected. To 120 µl of the supernatant collected, 30.1 of 5×SDS-PAGE Loading buffer was added, and the sample was boiled at 100° C. for 10 minutes, and stored at −20° C. for later use. Western blotting assay was carried out to detect anti-HER2 antibody expression using goat anti-human IgG (H+L) as primary antibody and HRP-rabbit-anti-goat antibody as secondary antibody, both purchased from Jackson ImmunoResearch. Results show that anti-HER2 antibody expressed by PIK-NK cells comprises the correct heavy chains (50 kD) and light chains (25 kD), as shown in FIG. 13.

Figure 14:
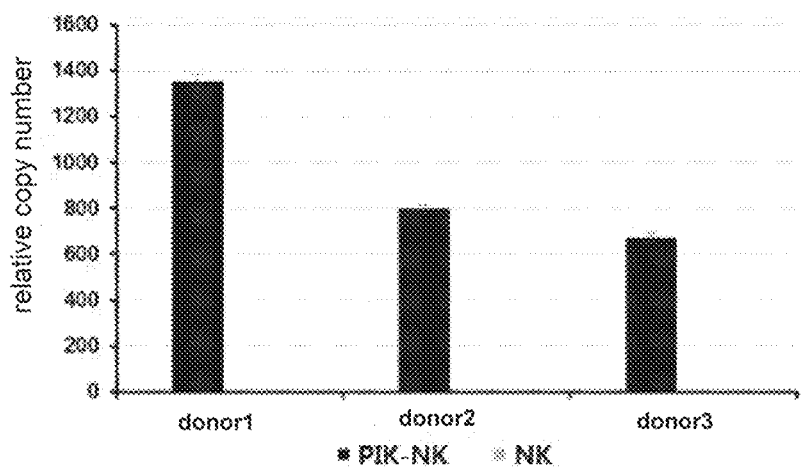
FIG. 14: The detection of HER2 antibody expression cassette in PIK-NK cell genome.

Example 16: Detection of Anti-HER2 Antibody Expression Cassette in PIK-NK Cell Genome Genomic DNA from PIK-NK cells obtained in Example 13 and control NK cells were extracted according to the manufacturer's instruction included in the kit. DNA concentrations of the PIK-NK cells and the control NK cells were measured by fluorescent real-time quantitative PCR with the following reaction program (primers as shown in SEQ ID NO:8 and SEQ ID NO:9): 95° C., 15 s→95° C., 5 s→60° C., 15 s, 40 cycles. Results show that the anti-HER2 antibody expression cassette is integrated into NK cell genome, as shown in FIG. 14.

```
F:
                                    (SEQ ID NO: 8)
GGCTGTCCTACAGTCCTCAG

R:
                                    (SEQ ID NO: 9)
TTGTCCACCTTGGTGTTGCT
```

Figure 15:
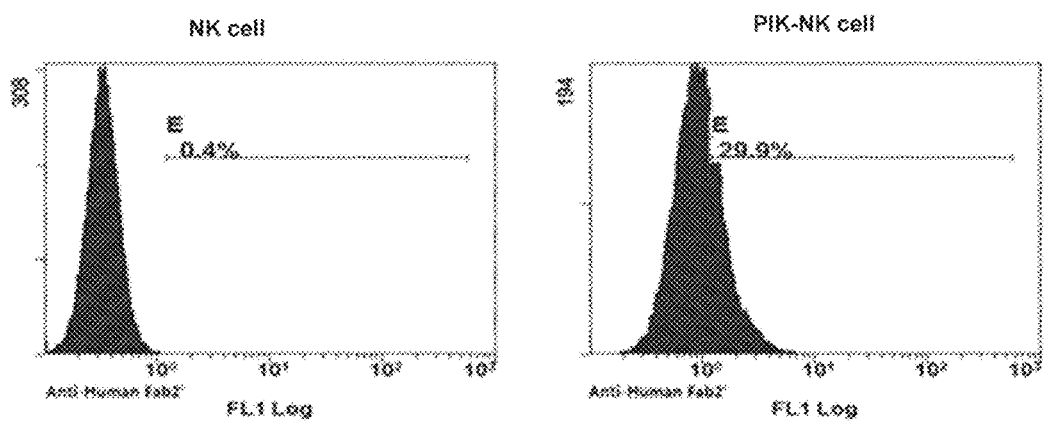
FIG. 15: Flow cytometry assay of antibody molecules expressed on the surface of PIK-NK cells.
Figure 16A:
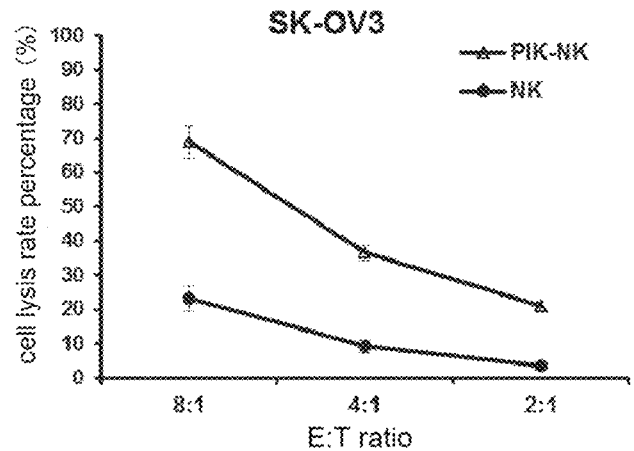
FIGS. 16A, 16B, 16C and 16D: The detection of in vitro cytotoxity of PIK-NK cells on different tumor cells.
Figure 16B:
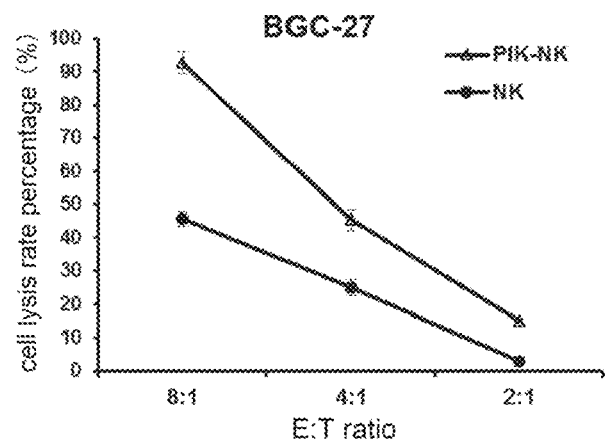
Figure 16C:
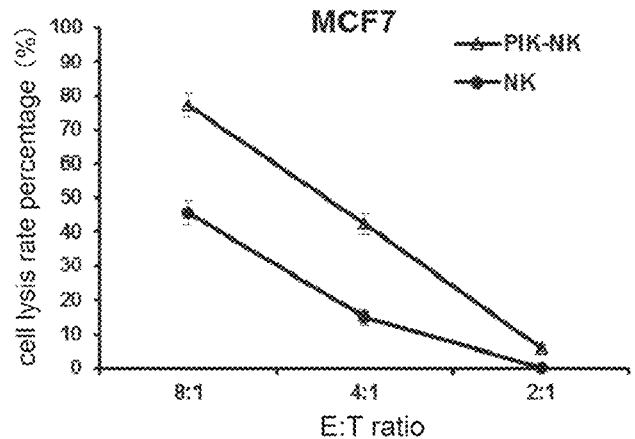
Figure 16D:
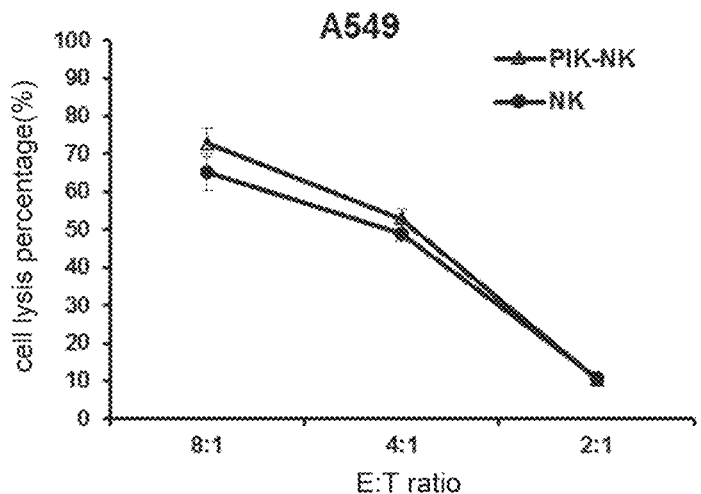

Example 17: Flow Cytometric Detection of Antibody Molecules on PIK-NK Cell Surface Suspended PIK-NK cells (obtained in example 13) and control NK cells were collected and counted before they were added into two 1.5 ml EP tubes at $1 \times 10^6$ cells/tube, respectively, washed twice with PBS and centrifuged at 1,200 rpm for 5 minutes. Supernatants were discarded, 2 µl of anti-human IgG Fab2'antibody (purchased from Jackson ImmunoResearch) was added. Pellets were tapped gently until well mixed, incubated for 30 minutes at room temperature in the dark, washed with PBS once, and centrifuged at 1,200 rpm for 5 minutes. Supernatants were discarded and 400 µl of normal saline was added before transferring the cells into flow cytometry tubes, and the sample was loaded onto flow cytometry device for detection. Experimental results show that compared to control cells, PIK-NK cells have anti-HER2 antibody molecules on their surface, as shown in FIG. 15.

Example 18: In Vitro Tumor Cell Killing Assay of PIK-NK Cells

HER2 positive tumor cell strains SK-OV3, BGC27 and MCF7 and HER2 negative tumor cell strain A549 (all purchased from American typical culture center, ATCC) were selected, and lactic dehydrogenase (LDH)-Cytotoxicity Assay Kit (Biovision) was used to detect the in vitro killing abilities of the NK cells with or without transgenes on different types of tumor cells. The effector, target ratios were set to 8:1, 4:1, and 2:1, respectively, and NK cells not transfected with plasmid were used as control (E:T=8:1), and cell proliferation curves were observed. Results show that compared to control cells, PIK-NK cells expressing anti-HER2 antibody (prepared in example 13) can kill HER2 positive tumor cells more efficiently, but has no significant killing effects on HER2 negative tumor cells, as shown in FIGS. 16A-16D.

Example 19: In Vivo Assay for Treating Tumor Xenograft with PIK-NK Cells

Figure 17:
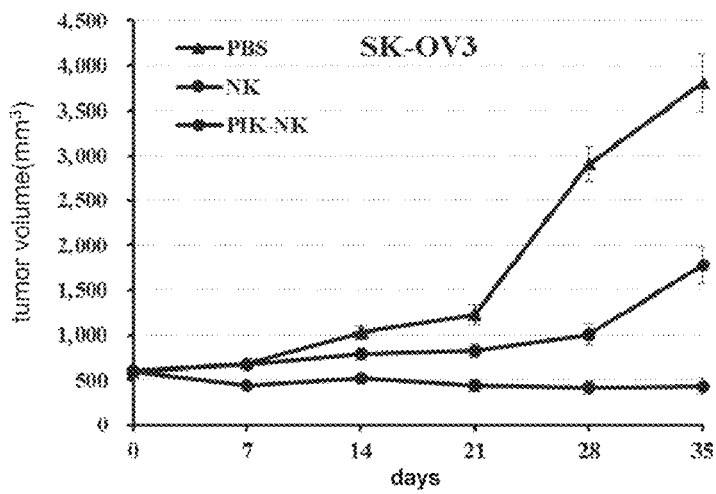
FIG. 17: The detection of in vivo inhibitory effects of PIK-NK cells on the transplanted tumor.

NOD-SCID mice (purchased from Shanghai SLAC Laboratory Animal Co., Ltd) were subcutaneously injected with $5 \times 10^6$ SK-OV3 malignant ovarian cancer cells. After 10 days, PIK-NK cells (prepared in Example 13), control NK cells (injection dosage $1 \times 10^7$) or PBS buffer were injected respectively via tail vein. The growth condition of the tumor xenograft was measured. Results show a significant difference between the inhibitory effects of PIK-NK cells and that of the control group on lung cancer (FIG. 17).

Example 20: In Vitro Clearance Assay of PIK-NK Cells (Validation of Molecular Brake Function)

Figure 18:
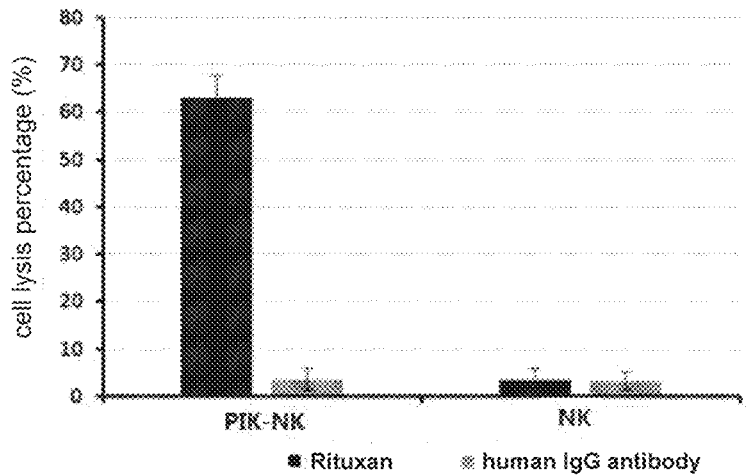
FIG. 18: Functional detection of the molecular brake system in PIK-NK cells.

PIK-NK cells obtained in Example 13 and NK cells were plated in 12-well plates supplemented with 4 ml of NK culture solution (purchased from STEMCELL Technologies) at the density of $1.0 \times 10^5$ cells/well, and 50 µg/ml Rituxan antibody or human IgG antibody were added, respectively. Lactic dehydrogenase (LDH)-Cytotoxicity Assay Kit (Biovision) was used to detect the lysis rate of PIK-NK cells after the addition of the antibodies. Results show that compared to control human IgG antibody, after adding Rituxan antibody, PIK-NK cells can be quickly lyzed; while NK cells do not have obvious response to Rituxan antibody or control human IgG antibody. The result indicates that since NK cells can highly efficiently mediate ADCC effect, after adding Rituxan antibody, they can bind to the CD20 epitope on the PIK-NK cell surface initiating the killing effects between cells, leading to the clearance of PIK-NK cells. This indicates that the CD20-Rituxan molecular brake system can effectively clear PIK-NK cells, which has good safety, as shown in FIG. 18.

Example 21: Construction of Recombinant Plasmid pNB328-herinCAR-PD1

HerinCAR coding sequence comprising CD20-Rituxan molecular brake as shown in SEQ ID NO: 10 (CAR targeting EGFR family, disclosed in CN201510812654.9) and herinCAR-PD1 coding sequence as shown in SEQ ID NO:11 (CAR targeting EGFR family and comprising CD20-Rituxan molecular brake and PD1 single chain-Fc antibody, linked by 2A) were synthesized by Shanghai Genray Biotech Co., Ltd, with EcoRI and SalI restriction sites introduced into its upstream and downstream, respectively, loaded into pNB328 vector, and were named pNB328-herinCAR and pNB328-herinCAR-PD1, respectively.

```
Coding sequence of herinCAR comprising CD20-Rituxan molecular brake:
                                                     (SEQ ID NO: 10)
GAATTCGCCACCATGGAGTTTTGGCTGAGCTGGGTTTTCCTTGTTGCTATTTAAAA

GGTGTCCAGTGTAACATATACAACTGTGAACCAGCTAATCCCTCTGAGAAAAACTC

CCCATCTACCCAATACTGTTACAGCATACAAGGTGGAGGTGGAGGTGGAGGTGGA

GGTGGTACCCACTCACTGCCCCCGAGGCCAGCTGCAGTTCCTGTCCCTCTGCGCAT

GCAGCCTGGCCCAGCCCACCCTGTCCTATCCTTCCTCAGACCCTCTTGGGACCTAGT

CTCTGCCTTCTACTCTCTACCCCTGGCCCCCCTCAGCCCTACAAGTGTCCCTATATC

CCCTGTCAGTGTGGGGAGGGGCCCGGACCCTGATGCTCATGTGGCTGTTGACCTGT

CCCGGTATGAAGGCGAGCCCAAATCTTGTGACAAAACTCACACATGCCCACCGTGC

CCAGCACCTGAGTTCGTGCCGGTCTTCCTGCCAGCGAAGCCCACCACGACGCCAGC

GCCGCGACCACCAACACCGGCGCCCACCATCGCGTCGCAGCCCCTGTCCCTGCGCC

CAGAGGCGTGCCGGCCAGCGGCGGGGGCGCAGTGCACACGAGGGGCTGGACTT

CGCCTGTGATATCTACATCTGGGCGCCCCTGGCCGGGACTTGTGGGGTCCTTCTCCT

GTCACTGGTTATCACCCTTTACTGCAACCACAGGAGTAAGAGGAGCAGGCTCCTGC

ACAGTGACTACATGAACATGACTCCCCGCCGCCCCGGGCCCACCCGCAAGCATTAC

CAGCCCTATGCCCCACCACGCGACTTCGCAGCCTATCGCTCCAGAGTGAAGTTCAG

CAGGAGCGCAGACGCCCCCGCGTACCAGCAGGGCCAGAACCAGCTCTATAACGAG

CTCAATCTAGGACGAAGAGAGGAGTACGATGTTTTGGACAAGAGACGTGGCCGGG

ACCCTGAGATGGGGGGAAAGCCGAGAAGGAAGAACCCTCAGGAAGGCCTGTACAA

TGAACTGCAGAAAGATAAGATGGCGGAGGCCTACAGTGAGATTGGGATGAAAGGC

GAGCGCCGGAGGGGCAAGGGGCACGATGGCCTTTACCAGGGTCTCAGTACAGCCA

CCAAGGACACCTACGACGCCCTTCACATGCAGGCCCTGCCCCCTCGCTGATAAGTC
GAC,
``` wherein double underline represents restriction sites, abd wave underline represents CD20 epitope coding sequence which is recognized by Rituxan antibody.

```
herinCAR-PD1 coding sequence:
                                                     (SEQ ID NO: 11)
GAATTCGCCACCATGGAGTTTTGGCTGAGCTGGGTTTTCCTTGTTGCTATTTTAAAA

GGTGTCCAGTGTAACATATACAACTGTGAACCAGCTAATCCCTCTGAGAAAAACTC

CCCATCTACCCAATACTGTTACAGCATACAAGGTGGAGGTGGAGGTGGAGGTGGA

GGTGGTACCCACTCACTGCCCCCGAGGCCAGCTGCAGTTCCTGTCCCTCTGCGCAT

GCAGCCTGGCCCAGCCCACCCTGTCCTATCCTTCCTCAGACCCTCTTGGGACCTAGT

CTCTGCCTTCTACTCTCTACCCCTGGCCCCCCTCAGCCCTACAAGTGTCCCTATATC

CCCTGTCAGTGTGGGGAGGGGCCCGGACCCTGATGCTCATGTGGCTGTTGACCTGT

CCCGGTATGAAGGCGAGCCCAAATCTTGTGACAAAACTCACACATGCCCACCGTGC
```

```
CCAGCACCTGAGTTCGTGCCGGTCTTCCTGCCAGCGAAGCCCACCACGACGCCAGC
GCCGCGACCACCAACACCGGCGCCCACCATCGCGTCGCAGCCCCTGTCCCTGCGCC
CAGAGGCGTGCCGGCCAGCGGCGGGGGCGCAGTGCACACGAGGGGGCTGGACTT
CGCCTGTGATATCTACATCTGGGCGCCCCTGGCCGGGACTTGTGGGGTCCTTCTCCT
GTCACTGGTTATCACCCTTTACTGCAACCACAGGAGTAAGAGGAGCAGGCTCCTGC
ACAGTGACTACATGAACATGACTCCCCGCCGCCCCGGGCCCACCCGCAAGCATTAC
CAGCCCTATGCCCCACCACGCGACTTCGCAGCCTATCGCTCCAGAGTGAAGTTCAG
CAGGAGCGCAGACGCCCCCGCGTACCAGCAGGGCCAGAACCAGCTCTATAACGAG
CTCAATCTAGGACGAAGAGAGGAGTACGATGTTTTGGACAAGAGACGTGGCCGGG
ACCCTGAGATGGGGGGAAAGCCGAGAAGGAAGAACCCTCAGGAAGGCCTGTACAA
TGAACTGCAGAAAGATAAGATGGCGGAGGCCTACAGTGAGATTGGGATGAAAGGC
GAGCGCCGGAGGGGCAAGGGGCACGATGGCCTTTACCAGGGTCTCAGTACAGCCA
CCAAGGACACCTACGACGCCCTTCACATGCAGGCCCTGCCCCTCGCCGTAAAAGG
CGAGCTCCTGTTAAACAGACTTTGAATTTTGACCTTCTCAAGTTGGCGGGAGACGT
CGAGTCCAACCCTGGGCCCATGGAAGCCCCAGCTCAGCTTCTCTTCCTCCTGCTACT
CTGGCTCCCAGATACCACCGGACAGGTGCAGCTGGTGCAGTCCGGCGTGGAGGTG
AAGAAGCCTGGCGCCTCCGTCAAGGTGTCCTGTAAGGCCTCCGGCTACACCTTCAC
CAACTACTACATGTACTGGGTGCGGCAGGCCCCAGGCCAGGGACTGGAGTGGATG
GGCGGCATCAACCCTTCCAACGGCGGCACCAACTTCAACGAGAAGTTCAAGAACC
GGGTGACCCTGACCACCGACTCCTCCACCACAACCGCCTACATGGAACTGAAGTCC
CTGCAGTTCGACGACACCGCCGTGTACTACTGCGCCAGGCGGGACTACCGGTTCGA
CATGGGCTTCGACTACTGGGGCCAGGGCACCACCGTGACCGTGTCCTCCGGTGGAG
GCGGTTCAGGCGGAGGTGGCAGCGGCGGTGGCGGGTCGGAAATTGTGTTGACACA
GTCTCCAGCCACCCTGTCTTTGTCTCCAGGGGAAAGAGCCACCCTCTCCTGCAGGG
CCAGCAAAGGTGTCAGTACATCTGGCTATAGTTATTTGCACTGGTATCAACAGAAA
CCTGGCCAGGCTCCCAGGCTCCTCATCTATCTTGCATCCTACCTAGAATCTGGCGTC
CCAGCCAGGTTCAGTGGTAGTGGGTCTGGGACAGACTTCACTCTCACCATCAGCAG
CCTAGAGCCTGAAGATTTTGCAGTTTATTACTGTCAGCACAGCAGGGACCTTCCGC
TCACGTTCGGCGGAGGGACCAAAGTGGAGATCAAAGAGTCCAAATATGGTCCCCC
ATGCCCACCATGCCCAGCACCTGAGTTCCTGGGGGGACCATCAGTCTTCCTGTTCCC
CCCAAAACCCAAGGACACTCTCATGATCTCCCGGACCCCTGAGGTCACGTGCGTGG
TGGTGGACGTGAGCCAGGAAGACCCCGAGGTCCAGTTCAACTGGTACGTGGATGG
CGTGGAGGTGCATAATGCCAAGACAAAGCCGCGGGAGGAGCAGTTCAACAGCACG
TACCGTGTGGTCAGCGTCCTCACCGTCCTGCACCAGGACTGGCTGAACGGCAAGGA
GTACAAGTGCAAGGTCTCCAACAAAGGCCTCCCGTCCTCCATCGAGAAAACCATCT
CCAAAGCCAAAGGGCAGCCCCGAGAGCCACAGGTGTACACCCTGCCCCCATCCCA
GGAGGAGATGACCAAGAACCAGGTCAGCCTGACCTGCCTGGTCAAAGGCTTCTAC
CCCAGCGACATCGCCGTGGAGTGGGAGAGCAATGGGCAGCCGGAGAACAACTACA
AGACCACGCCTCCCGTGCTGGACTCCGACGGCTCCTTCTTCCTCTACAGCAGGCTA
```

```
ACCGTGGACAAGAGCAGGTGGCAGGAGGGGAATGTCTTCTCATGCTCCGTGATGC

ATGAGGCTCTGCACQAACCACTACACACAGAAGAGCCTCTCCCTGTCTCTGGGTAAA

TGATAAGTCGAC,
``` wherein double underline represents restriction sites, single underline represents the coding sequence of Furin 2A, wavy underline represents CD20 epitope coding sequence recognized by Rituxan antibody, dashed underline represents IgG4 hinge coding sequence, and double-wave underline represents IgG4 Fc coding sequence.

Figure 19:
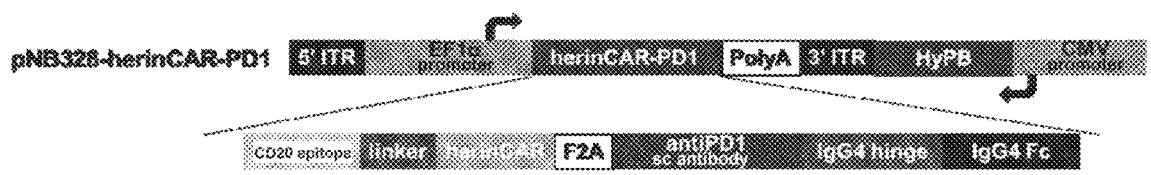
FIG. 19: A schematic diagram of the expression cassette of herinCAR-PD1. ITR is a transposon's inverted terminal repeat sequence; HyPB is a piggybac transposase. Hinge is an antibody's hinge.

The schematic diagram of pNB328-herinCAR-PD1 vector is shown in FIG. 19.

Example 22: Construction of herinCAR-PD1 Cells $1\times10^7$ freshly isolated peripheral blood mononuclear cell (PBMC) were prepared. 6 μg of pNB328-herinCAR-PD1 plasmid was transfected into cell nucleus by Lonza 2b-Nucleofector. The cells were incubated at 37° C., 5% $CO_2$ in an incubator. After 6 hours, the cells were transferred to a 6-well plate containing 30 ng/ml anti-CD3 antibody and 3000 IU/ml IL-2 (purchased from Novoprotein), and incubated at 37° C., 5% $CO_2$ in an incubator. When reaching confluency, cells were passaged at a split ratio of 1:5 to obtain genetically modified T cells that co-express CAR targeting EGFR family comprising CD20-Rituxan molecular brake and anti-PD1 single chain-Fc antibody (abbreviated as herinCAR-PD1 cells). Meanwhile, herinCAR-T cells were obtained by transfecting PBMCs from the same donors with pNB328-herinCAR plasmid.

Example 23: Quantitative Assay of the Amount of Anti-PD1 Antibody Expression in herinCAR-PD1 Cells Cells obtained in Example 22 and herinCAR cells were passaged at a split ratio of 1:3. After two weeks, they were plated in 6-well plates supplemented with 4 ml of AIM-V culture solution (purchased from GIBCO) at the density of $1.0\times10^6$ cells/well and incubated at 37° C., 5% $CO_2$ in an incubator. After incubating for 24 hours, 48 hours, 72 hours and 96 hours, 800 μl of cell-containing supernatant was collected and stored at −20° C. for later use. ELISA plates (purchased from SinoBiological) were coated with recombinant human PD1 protein, and HRP-labeled mouse anti-human IgG mAb (purchased from Abcam) was used for the assay, with commercialized anti-PD1 antibody (purchased from Merck) as reference standard. The amount of PD1 antibody expression was measured by double-sandwich ELISA.

Figure 20:
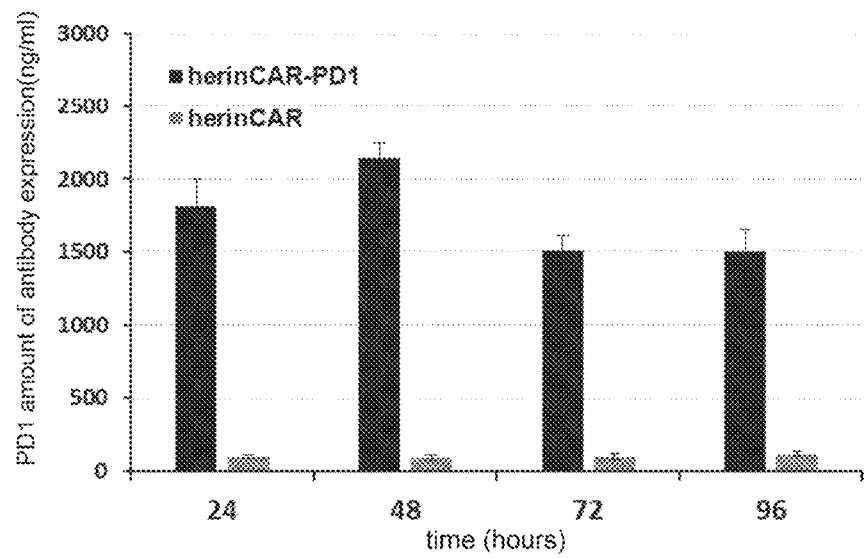
FIG. 20: ELISA assay of PD1 antibody expression levels in herinCAR-PD1 cells. The control is herinCAR cells.

Results show that herinCAR-PD1 cells can stably express high level of PD1 antibody, specifically as shown in FIG. 20.

Figure 21:
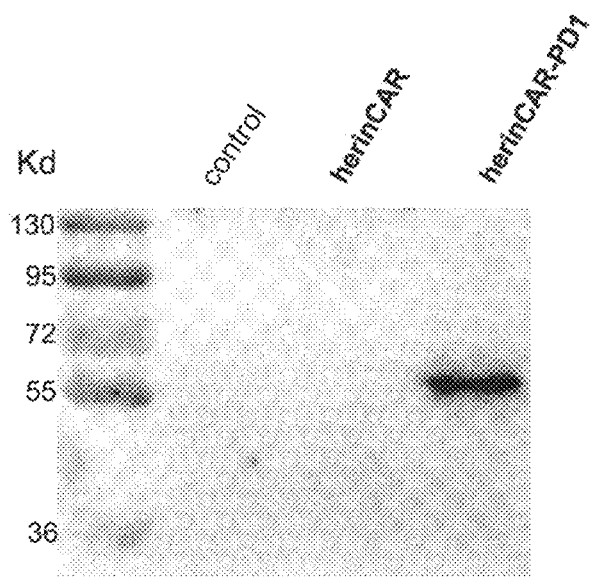
FIG. 21: Western blotting assay of the expression of PD1 antibody in herinCAR-PD1.

Example 24: Qualitative Assay of the Expression of Anti-PD1 Antibody in herinCAR-PD1 Cells HerinCAR-PD1 cells obtained in Example 22 were plated in 6-well plates supplemented with 4 ml of AIM-V culture solution at the density of $1.0\times10^6$ cells/well and incubated at 37° C., 5% $CO_2$ in an incubator. After incubating for 48 hours, cell-containing supernatant was collected. To 120 μl of supernatant 30 μl of 5×SDS-PAGE Loading buffer was added, and the sample was boiled at 100° C. for 10 minutes, and stored at −20° C. for later use. Western blotting assay was carried out to detect anti-PD1 antibody expression using goat anti-human IgG (H+L) as primary antibody and HRP-rabbit-anti-goat antibody as secondary antibody, both purchased from Jackson ImmunoResearch. Results show that anti-PD1 antibody expressed by herinCAR-PD1 cells comprises the correct scFv-Fc antibody (52 kD), as shown in FIG. 21.

Example 25: Proliferation Assay of herinCAR-PD1 Cells

Figure 22:
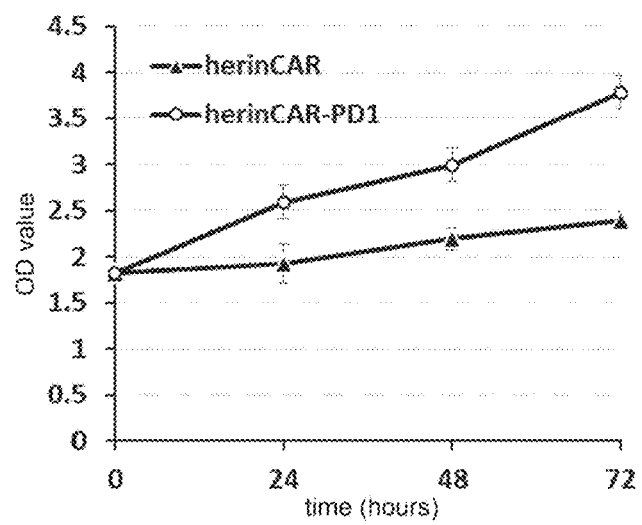
FIG. 22: Cell proliferation assay of herinCAR-PD1 cells.

HerinCAR-PD1 cell obtained in Example 22 and herinCAR cells were plated in 96-well plates at the density of $4\times10^4$ cells/well (each cell type in triplicate, with a total volume of 200 μl), and incubated at 37° C., 5% $CO_2$ in an incubator. After incubating for 24 hours, 48 hours, 72 hours and 96 hours, 20 μl of CCK8 reagent was added, and the sample was incubated for 6 hours at 37° C. in the dark. The $OD_{450}$ value was measured on an ELISA analyzer. Results show that the proliferation speed of herinCAR-PD1 cells is significantly higher than that of herinCAR control, indicating that the antibody secreted by herinCAR-PD1 cells can promote the proliferation of T cells, specifically as shown in FIG. 22.

Example 26: In Vitro Killing Assay of herinCAR-PD1 Cells

Figure 23A:
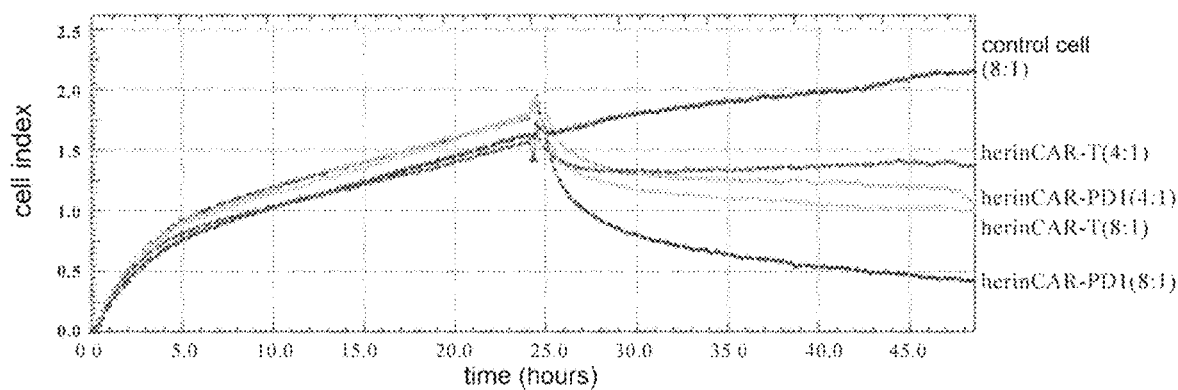
FIGS. 23A, 23B, and 23C: The detection of in vitro cytotoxity of herinCAR-PD1 cells on tumor cells. E:T, effector to target ratio.
Figure 23B:
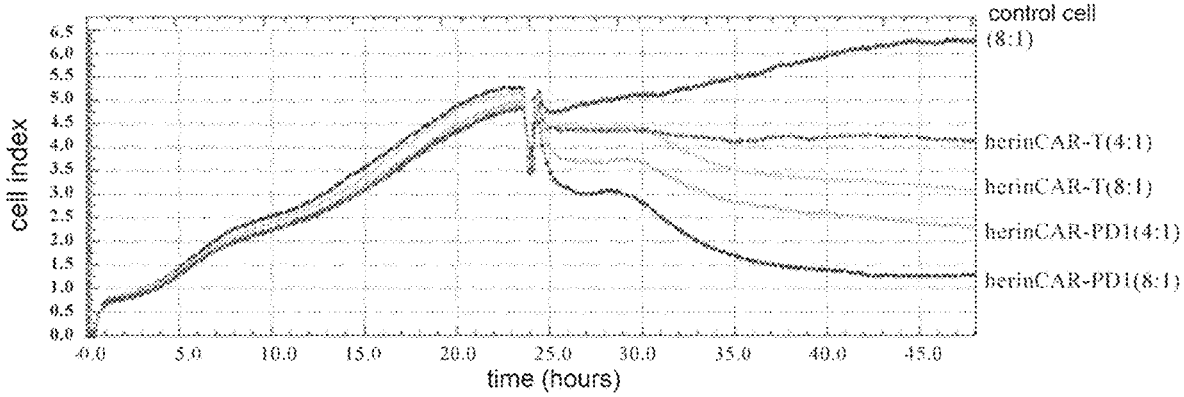
Figure 23C:
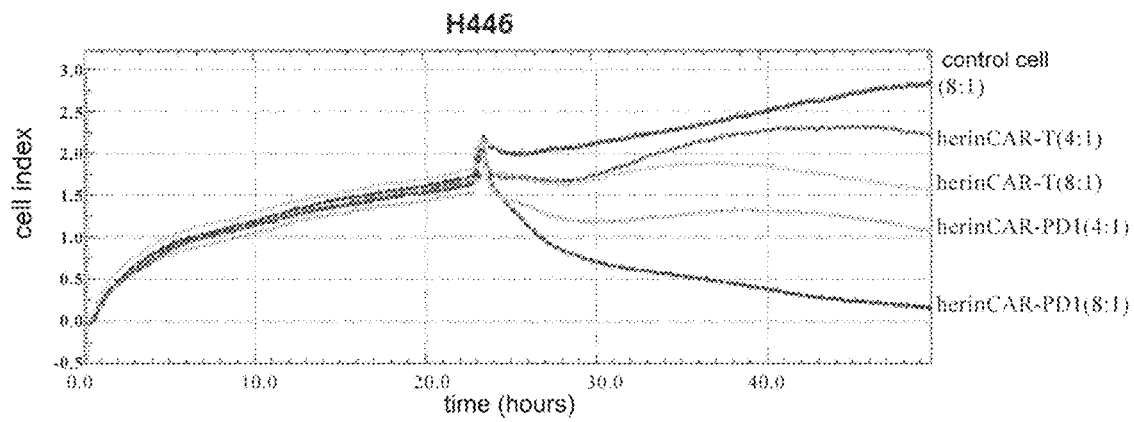

Lung cancer cell strains NCI-H23, H446, H460 and H1299 (purchased from American typical culture center. ATCC) were plated on RTCA cell proliferation plates (purchased from ACEA Biosciences, USA) at the ratio of 10,000/well. The plates were placed on xCELLigence RTCA DP multi-functional real-time unlabeled cell analyzer to record the real-time growth of the cells (indicated by the cell index measured, higher value means that the cells are in a better state). After 24 hours, herinCAR cells and herinCAR-PD1 cells constructed in Example 22 were added respectively with effector:target ratio (E:T) at 4:1 and 2:1. The plates are placed again on xCELLigence RTCA DP multi-functional real-time unlabeled cell analyzer to record the real-time growth of the cells. Results show that compared to herinCAR-T cells not expressing anti-PD1 antibody, herinCAR-T cells expressing anti-PD1 antibody, that is, herinCAR-PD1 cells have significantly improved cytotoxicity to lung cancer cells (FIGS. 23A-C). The above results indicate that the co-expression of anti-PD1 antibody can improve the cytotoxicity of CAR-T cells to lung cancer cells.

Figure 24:
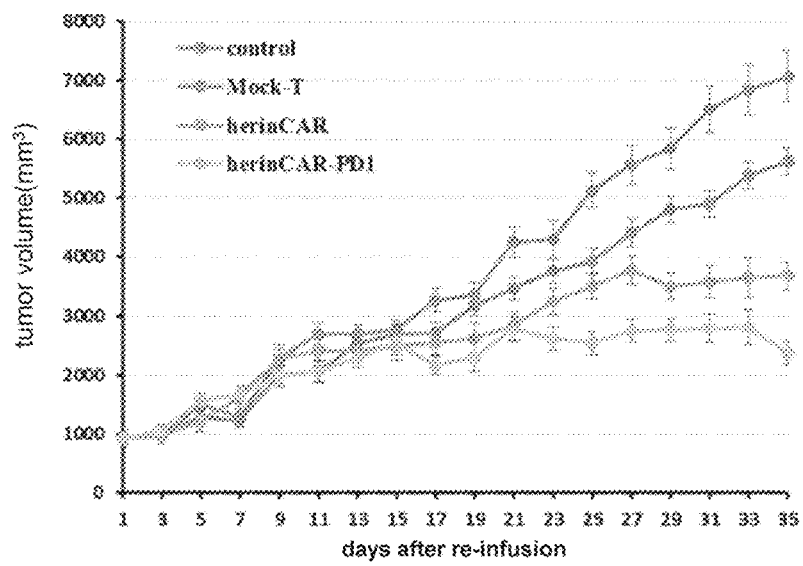
FIG. 24: The detection of in vivo inhibitory effects of herinCAR-PD1 cells on transplanted tumor. Control, PBS treatment group, Mock-T, non-transgenic T cells.

Example 27: Identification of In Vivo Killing Activity of herinCAR-PD1 Cells NOD-SCID mice (purchased from Shanghai SLAC Laboratory Animal Co., Ltd) were subcutaneously injected with $5\times10^6$ Huh7 malignant liver cancer cells. After 10 days, herinCAR cells, herinCAR-PD1 cells prepared in Example 22 and T cells without transgenes from the same donor (dosage of injection $2\times10^5$) or PBS buffer were injected via tail vein, respectively. The state of growth of the tumor xenograft was measured. Results show a significant difference between the inhibitory effects of herinCAR-PD1 cells on liver cancer and that of the control group (FIG. 24). HerinCAR-T cells with co-expression of anti-PD1 antibody shows excellent in vivo anti-tumor effect.

Example 28: Proliferation Assay of herinCAR-PD1 Cells in Tumor Xenograft

Figure 25:
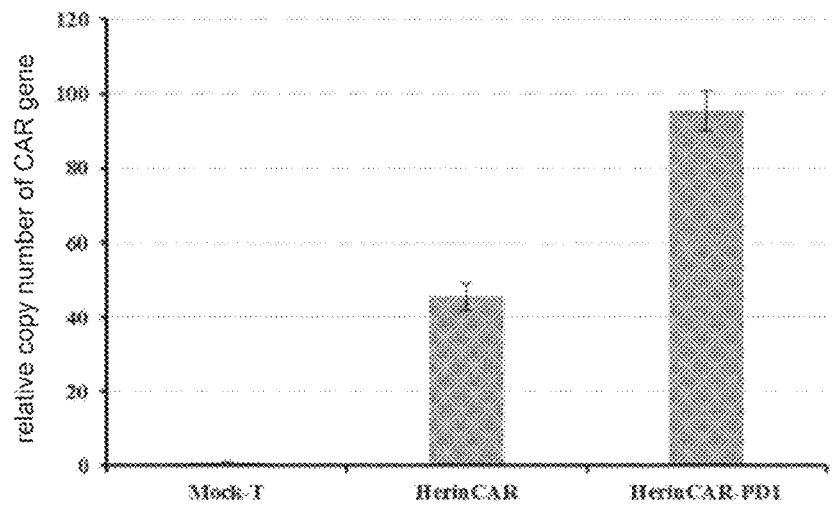
FIG. 25: Proliferation of HerinCAR-PD1 cells in the transplanted tumor. Mock-T is non-transgenic T cells.

Thirty-five days after the treatment in Example 27, the tumor-bearing mice were killed. The tumor xenograft tissues were retrieved and genomic DNA was extracted (operated according to the tissue DNA extraction kit of Sigma-Aldrich company). Relative copy number of herinCAR gene in the tumor xenograft was detected by RT-PCR (primers as shown in SEQ ID NO: 12 and SEQ ID NO: 13, the reaction system and the program were operated according to the RealMaster Mix (SYBR Green) detection kit from TIANGEN BIOTECH). Results show that compared to herinCAR-T cells, the copy number of herinCAR-PD1 cells in tumor xenograft is remarkably increased, indicating that the expression of anti-PD1 antibody can extend the survival Lime of CAR-T cells in tumor xenograft (FIG. 25).

```
F:
                                          (SEQ ID NO: 12)
CAGTGAGATTGGGATGAAAGG;

R:
                                          (SEQ ID NO: 13)
GAAGGGCGTCGTAGGTGTC
```

Example 29: In Vivo Clearance Assay of herinCAR-PD1 Cells (Validation of Molecular Brake Function)

BABL/c nude mice (purchased from Shanghai SLAC Laboratory Animal Co., Ltd) were injected with the herinCAR-PD1 cells prepared in Example 22 via tail vein (dosage of injection 5×10$^6$). After 3 days, 100 μg of Rituxan antibody or human IgG control antibody were injected intravenously. After 12 hours, blood and bone marrow samples were collected and the proportion of CAR-T cells was detected using flow cytometry.

Figure 26:
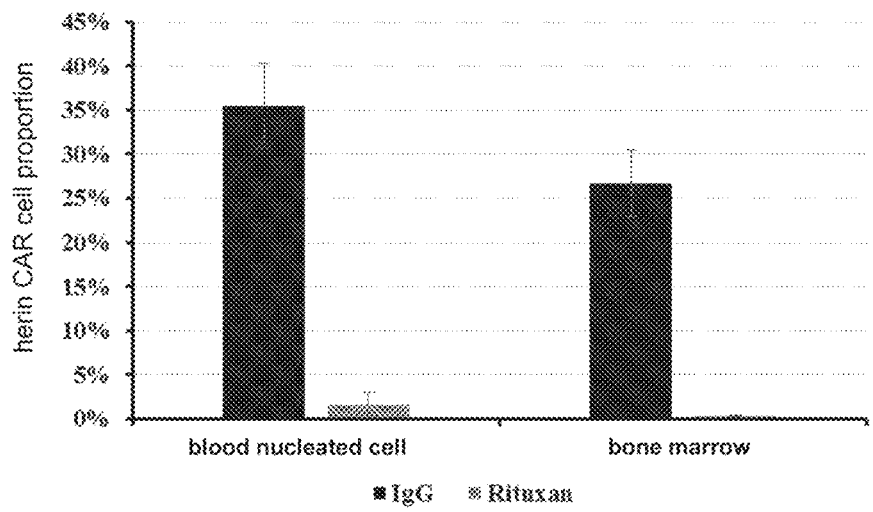
FIG. 26: Functional detection of the molecular brake system in HerinCAR-PD1 cells.

The results showed that the ratio of infused HERINCAR-PD1 cells in blood to bone marrow was significantly lower after injection of rituximab antibody compared to the control group injected with human IgG antibody (FIG. 26). It can be seen that the CD20 molecular brake can effectively function in the body, and the herinCAR-PD1 cells containing the CD20 epitope can be cleared by the ADCC and CDC effects.

Example 30: Construction of Recombinant Plasmid pNB328-herinCAR-CD28

HerinCAR-CD28 coding sequence as shown in SEQ ID NO: 14 (CAR targeting EGFR family and comprising CD20-Rituxan molecular brake and CD28 single chain-membrane binding antibody, linked by 2A) was synthesized by Shanghai Genray Biotech Co., Ltd, with EcoRI and SalI restriction sites introduced into its upstream and downstream, respectively, loaded into pNB328 vectors, and were named pNB328-herinCAR and pNB328-herinCAR-CD28, respectively.

```
herinCAR-CD28 coding sequence:
                                          (SEQ ID NO: 14)
GAATTCGCCACCATGGAGTTTTGGCTGAGCTGGGTTTTCCTTGTTGCTAT

TTTAAAAGGTGTCCAGTGTAACATATACAACTGTGAACCAGCTAATCCCTCTGAGA

AAAACTCCCCATCTACCCAATACTGTTACAGCATACAAGGTGGAGGTGGAGGTGGA

GGTGGAGGTGGTACCCACTCACTGCCCCCGAGGCCAGCTGCAGTTCCTGTCCCTCT

GCGCATGCAGCCTGGCCCAGCCCACCCTGTCCTATCCTTCCTCAGACCCTCTTGGGA

CCTAGTCTCTGCCTTCTACTCTCTACCCCTGGCCCCCCTCAGCCCTACAAGTGTCCC

TATATCCCCTGTCAGTGTGGGGAGGGGCCCGGACCCTGATGCTCATGTGGCTGTTG

ACCTGTCCCGGTATGAAGGCGAGCCCAAATCTTGTGACAAAACTCACACATGCCCA

CCGTGCCCAGCACCTGAGTTCGTGCCGGTCTTCCTGCCAGCGAAGCCCACCACGAC

GCCAGCGCCGCGACCACCAACACCGGCGCCCACCATCGCGTCGCAGCCCCTGTCCC

TGCGCCCAGAGGCGTGCCGGCCAGCGGCGGGGGCGCAGTGCACACGAGGGGGCT

GGACTTCGCCTGTGATATCTACATCTGGGCGCCCCTGGCCGGGACTTGTGGGGTCC

TTCTCCTGTCACTGGTTATCACCCTTTACTGCAACCACAGGAGTAAGAGGAGCAGG

CTCCTGCACAGTGACTACATGAACATGACTCCCCGCCGCCCCGGGCCCACCCGCAA

GCATTACCAGCCCTATGCCCCACCACGCGACTTCGCAGCCTATCGCTCCAGAGTGA

AGTTCAGCAGGAGCGCAGACGCCCCCGCGTACCAGCAGGGCCAGAACCAGCTCTA

TAACGAGCTCAATCTAGGACGAAGAGAGGAGTACGATGTTTTGGACAAGAGACGT

GGCCGGGACCCTGAGATGGGGGGAAAGCCGAGAAGGAAGAACCCTCAGGAAGGC

CTGTACAATGAACTGCAGAAAGATAAGATGGCGGAGGCCTACAGTGAGATTGGGA
```

```
TGAAAGGCGAGCGCCGGAGGGGCAAGGGGCACGATGGCCTTTACCAGGGTCTCAG

TACAGCCACCAAGGACACCTACGACGCCCTTCACATGCAGGCCCTGCCCCCTCGCC

GTAAAAGGCGAGCTCCTGTTAAACAGACTTTGAATTTTGACCTTCTCAAGTTGGCG

GGAGACGTCGAGTCCAACCCTGGGCCCATGGAGTTTTGGCTGAGCTGGGTTTTCT

TGTTGCTATTTTAAAAGGTGTCCAGTGTCAGGTGCAGCTGGTGCAGTCTGGGCTG

AGGTGAAGAAGCCTGGGGCCTCAGTGAAGGTCTCCTGCAAGGCTTCTGGATACACC

TTCACCAGCTACTATATACACTGGGTGCGACAGGCCCCTGGACAAGGGCTTGAGTG

GATTGGATGTATTTATCCTGGAAATGTCAATACTAACTATAATGAGAAGTTCAAGG

ACAGGGCCACCCTGACCGTAGACACGTCCATCAGCACAGCCTACATGGAGCTGAG

CAGGCTGAGATCTGACGACACGGCCGTGTATTTCTGTACAAGATCACACTACGGCC

TCGACTGGAACTTCGATGTCTGGGGCCAAGGGACCACGGTCACCGTCTCCTCAGGT

GGAGGCGGTTCAGGCGGAGGTGGCAGCGGCGGTGGCGGGTCGGACATCCAGATGA

CCCAGTCTCCATCCTCCCTGTCTGCATCTGTAGGAGACAGAGTCACCATCACTTGCC

ATGCCAGTCAAAACATTTATGTTTGGTTAAACTGGTATCAGCAGAAACCAGGGAAA

GCCCCTAAGCTCCTGATCTATAAGGCTTCCAACCTGCACACAGGGGTCCCATCAAG

GTTCAGTGGCAGTGGATCTGGGACAGATTTCACTCTCACCATCAGCAGTCTGCAAC

CTGAAGATTTTGCAACTTACTACTGTCAACAGGGTCAAACTTATCCGTACACGTTCG

GCGGAGGGACCAAGGTGGAGATCAAAATTGAAGTTATGTATCCTCCTCCTTACCTA

GACAATGAGAAGAGCAATGGAACCATTATCCATGTGAAAGGGAAACACCTTTGTC

CAAGTCCCCTATTTCCCGGACCTTCTAAGCCCTTTTGGGTGCTGGTGGTGGTTGGTG

GAGTCCTGGCTTGCTATAGCTTGCTAGTAACAGTGGCCTTTATTATTTTCTGGGTGA

GGAGTAAGTGATAAGTCGAC,
``` wherein double underline represents restriction sites, single underline represents Furin 2A coding sequence, and dashed underline represents CD28 single chain antibody coding sequence.

Figure 27:
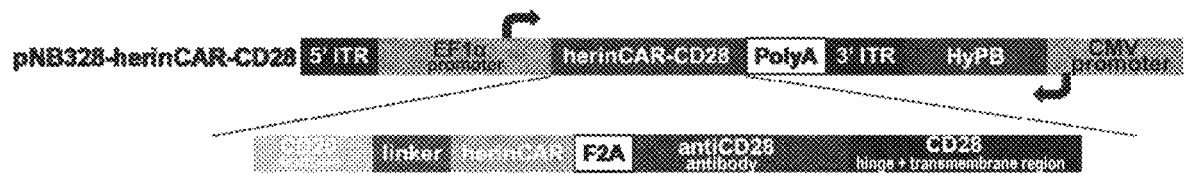
FIG. 27: A schematic diagram of the expression cassette of herinCAR-CD28. ITR is a transposon's inverted terminal repeat sequence; HyPB is a piggybac transposase.

The schematic diagram of pNB328-herinCAR-CD28 vector is shown in FIG. 27.

Example 31: Construction of herinCAR-CD28 Cells $1 \times 10^7$ freshly isolated peripheral blood mononuclear cell (PBMC) were prepared. 6 µg of pNB328-herinCAR-CD28 plasmid was transfected into cell nucleus by Lonza 2b-Nucleofector. The cells were incubated at 37° C., 5% $CO_2$ in an incubator for 6 hours, and then transferred to a 6-well plate containing 30 ng/ml anti-CD3 antibody and 3000 IU/ml IL-2 (purchased from Novoprotein), and incubated at 37° C., 5% $CO_2$ in an incubator. After the cells had grown to confluency, they were passaged at a split ratio of 1:5 to obtain genetically modified T cells that express both EGFR family targeting-CAR with CD20-Rituxan molecular brake, and CD28 single chain antibody, abbreviated as herinCAR-CD28 cells. Meanwhile, PBMC from the same donor was transfected with pNB328-herinCAR plasmid to obtain herinCAR-T cells.

Figure 28:
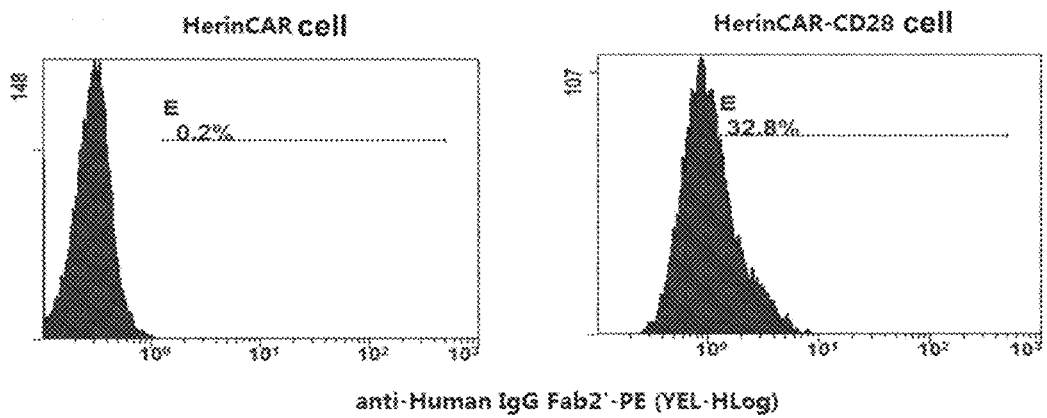
FIG. 28: Flow cytometry assay of CD28 antibody molecules expressed on herinCAR-CD28 cell surface. The control is herinCAR cells.

Example 32: Detection of Anti-CD28 Antibody Molecules on herinCAR-CD28 Cell Surface Suspended herinCAR-CD28 cells (constructed in Example 31) and control herinCAR-T cells were collected and counted, and then added into two 1.5 ml EP tubes, respectively at the density of $1 \times 10^6$ cells/tube, washed twice with PBS and centrifuged at 1,200 rpm for 5 minutes. Supernatants were discarded, and 2 µl of anti-human IgG Fab2' antibody (purchased from Jackson ImmunoResearch) was added. Pellets were tapped gently until well mixed, incubated for 30 minutes at room temperature in the dark, washed with PBS once, and centrifuged for 5 minutes at 1.200 rpm. Supernatants were discarded. 400 µl of normal saline was added before transferring the cells into flow cytometry tubes, and loaded onto the flow cytometry device for detection. Experimental results show that compared to control cells, herinCAR-CD28 cells have anti-CD28 antibody molecules on the surface, specifically as shown in FIG. 28.

Example 33: Detection of CD28 Molecules on herinCAR-CD28 Cell Surface

Figure 29:
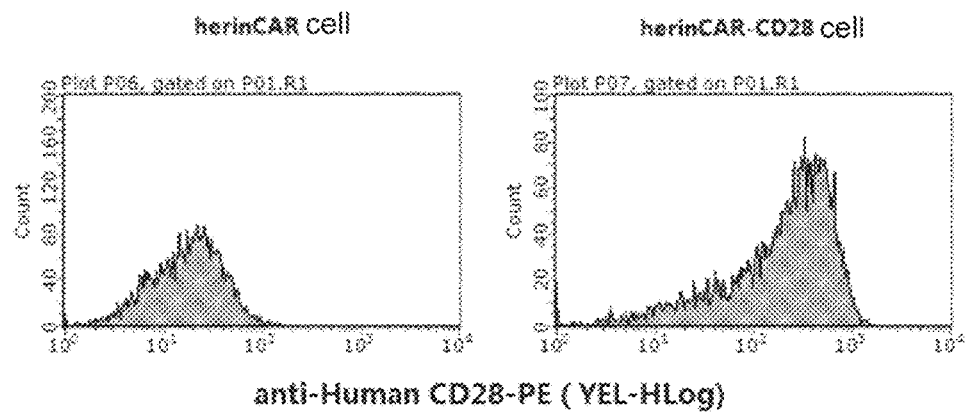
FIG. 29: Flow cytometry assay of CD28 molecules on herinCAR-CD28 cell surface.

Suspended herinCAR-CD28 cells (constructed in Example 31) and control herinCAR-T cells were collected and counted, and then added into two 1.5 ml EP tubes, respectively, at the density of $1\times10^6$ cells/tube, washed twice with PBS and centrifuged at 1,200 rpm for 5 minutes. Supernatants were discarded, and 2 μl of isotype control antibody IgG I-PE and anti-CD28-PE antibodies (both purchased from BD) were added, respectively. Pellets were tapped gently until well mixed, incubated for 30 minutes at room temperature in the dark, washed with PBS once, centrifuged for 5 minutes at 1,200 rpm. Supernatants were discarded, and 400 μl of normal saline was added before transferring the cells into flow cytometry tubes, and loaded onto the flow cytometry device for detection. Experimental results show that compared to control herinCAR cells, the CD28 positive rate is significantly increased in herinCAR-CD28 cells, indicating that herinCAR-CD28 cells can effectively activate CD28 signal of adjacent T cells through anti-CD28 antibody on the membrane surface thereof, specifically as shown in FIG. 29.

Figure 30:
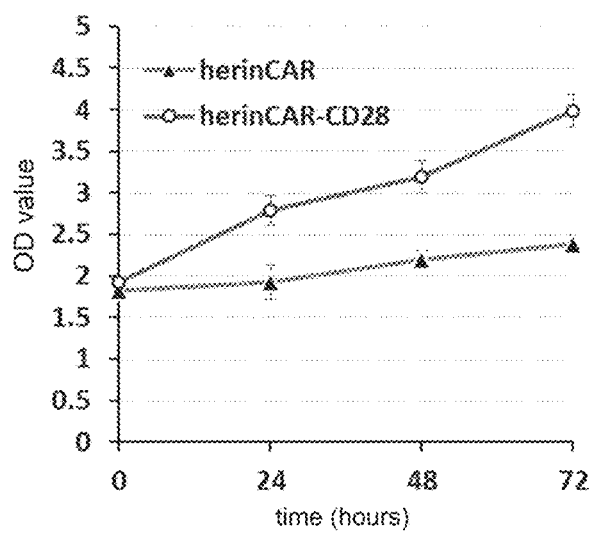
FIG. 30: Cell proliferation assay of herinCAR-CD28 cells.

Example 34: Proliferation Assay of herinCAR-CD28 Cells herinCAR-CD28 cell and herinCAR cells constructed in Example 31 were plated in 96-well plates at the density of $4\times10^4$ cells/well (each cell type in triplicate, with a total volume of 200 μl), and incubated at 37° C., 5% $CO_2$ in an incubator. After the cells were incubated for 24 hours, 48 hours, 72 hours and 96 hours, 20 μl of CCK8 reagent was added, and the sample was incubated for 6 hours at 37° C. in the dark. The $OD_{450}$ value was measured on an ELISA analyzer. Results show that the proliferation speed of herinCAR-CD28 cells is significantly higher than that of herinCAR control cells, indicating that anti-CD28 antibody on herinCAR-CD28 cell membrane surface can promote the proliferation of T cells, specifically as shown in FIG. 30.

Example 35: In Vitro Killing Activity Assay of herinCAR-CD28 Cells

Figure 31:
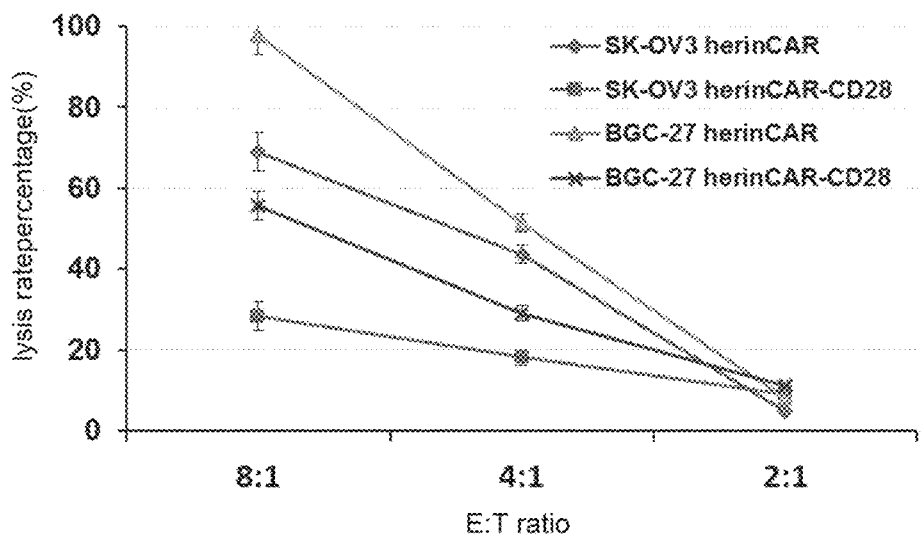
FIG. 31: The detection of in vitro cytotoxity of herinCAR-CD28 cells on tumor cells. E:T effector to target ratio.

Gastric cancer cell strain BGC-27 and ovarian cancer strain SK-OV3 (purchased from American typical culture center, ATCC) were plated on RTCA cell proliferation plates (purchased from ACEA Biosciences, USA) at a ratio of 10,000/well. The plates were placed on xCELLigence RTCA DP multi-functional real-time unlabeled cell analyzer to record the real-time growth of the cells (indicated by the cell index measured, the higher means that the cell is in better state). After 24 hours, herinCAR cells and herinCAR-CD28 cells constructed in Example 31 were added, respectively, with effector: target (E:T) ratio at 8:1, 4:1, 2:1 and 0:1. The plates were placed again on xCELLigence RTCA DP multi-functional real-time unlabeled cell analyzer to record the real-time growth of the cells. After 48 h, tumor cell lysis rate was determined according to the ratio of cell index under each E:T ratio to the corresponding cell index under 0:1 E:T rate (without effector cells). Results show that compared to herinCAR-T cells not expressing anti-CD28 antibody, the herinCAR-T cells expressing anti-CD28 antibody, that is, herinCAR-CD28 cells have significantly improved killing activity for BGC-27 and SK-OV3 cells (FIG. 31). The above results indicate that the co-expression of CD28 antibody can improve the killing activity of CAR-T cells for tumor cells.

Example 36: Identification of In Vivo Killing Activity of herinCAR-CD28 Cells

Figure 32:
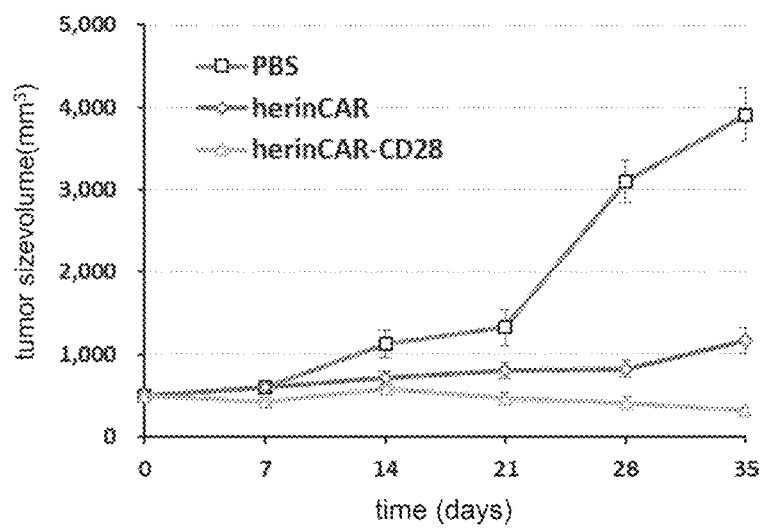
FIG. 32: The detection of in vivo inhibitory effects of herinCAR-CD28 cells on the transplanted tumor.

NOD-SCID mice (purchased from Shanghai SLAC Laboratory Animal Co., Ltd) were subcutaneously injected with $5\times10^6$ BGC-27 malignant gastric cancer cells. After 10 days, herinCAR cells, herinCAR-CD28 cells prepared in Example 31 (dosage of injection $2\times10^5$) or PBS buffer were injected, respectively, via tail vein. The state of growth of the tumor xenograft was measured. Results show a significant difference between the inhibitory effects of herinCAR-CD28 cells on liver cancer and that of the control group (FIG. 32), indicating that herinCAR-T cells with CD28 co-expression have excellent in vivo anti-tumor effects.

Example 37: Proliferation Assay of herinCAR-CD28 Cells in Tumor Xenograft

Figure 33:
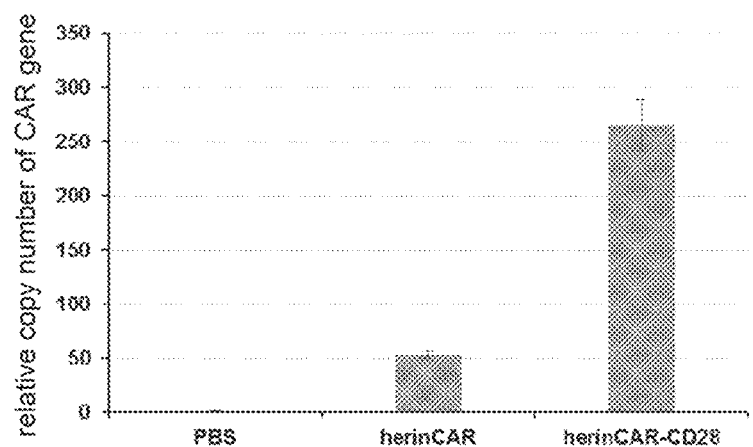
FIG. 33: Detection of proliferation of HcrinCAR PD1 HerinCAR-CD28 cells in transplanted tumors.

Thirty-five days after the treatment of example 36, the tumor-bearing mice were killed, tumor xenograft tissues were retrieved and genomic DNA was extracted (operated according to the tissue DNA extraction kit of Sigma-Aldrich company). Relative copy number of herinCAR gene in the tumor xenograft was detected by RT-PCR (primers as shown in SEQ ID NO: 12 and SEQ ID NO: 13, the reaction system and the program were set according to the RealMaster Mix (SYBR Green) detection kit from TIANGEN BIOTECH). Results show that compared to herinCAR-T cells, the copy number of herinCAR-CD28 cells in tumor xenograft is remarkably increased (FIG. 33), indicating that the expression of anti-CD28 antibody can extend the survival time of CAR-T cells in tumor xenograft.

Although specific embodiments of the present invention have been described in detail, those skilled in the art will appreciate that various modifications and substitutions may be made to those details in accordance with all of the teachings that have been disclosed, and all the modifications are within the protection scope of the invention. The scope of the invention is given by the appended claims and any equivalent thereof.

The invention claimed is:

1. A transgenic killer cell, wherein the genome of the killer cell is stably integrated with an expression cassette comprising a nucleotide sequence of SEQ ID NO: 11 or 14, each encoding an antibody, wherein both ends of the expression cassette further comprise inverted terminal repeat sequences of a transposon.

2. The transgenic killer cell of claim 1, wherein the amount of antibody expressed per million of said killer cells in 48 hours is higher than 2 μg.

3. The transgenic killer cell of claim 1, wherein the transposon is selected from the group consisting of
piggybac;
sleeping beauty;
frog prince;
Tn5; and
Ty.

4. The transgenic killer cell of claim 1, wherein the killer cell is selected from the group consisting of
a cytokine-induced killer cell;
a dendritic cell-stimulated cytokine-induced killer cell;
a cytotoxic T lymphocyte;
γδT cells;
natural killer cells;
NKT cells;
tumor infiltrating lymphocytes;
lymphokine activated killer cells;
anti-CD3 mAb killer cells;
genetically modified CAR-T;
genetically modified CAR-NK; and
genetically modified TCR-T cells.

5. A transgenic killer cell,
wherein the genome of the transgenic killer cell is stably integrated with a nucleic acid construct C, wherein the nucleic acid construct C comprises:
a transposon 5' inverted terminal repeat sequence (5' ITR),
a nucleic acid sequence of SEQ ID NO:11 or 14, each encoding an antibody,
a nucleic acid sequence encoding a promoter controlling the expression of SEQ ID NO:11 or 14,
a polyA tailing signal sequence,
a transposon 3' inverted terminal repeat sequence (3' ITR),
a transposase coding sequence, and
a promoter controlling the expression of the transposase coding sequence.

6. A pharmaceutical composition comprising the transgenic killer cell of claim 1 and a pharmaceutically acceptable excipient.

7. The transgenic killer cell according to claim 5, wherein the nucleic acid construct C is transformed into the transgenic killer cell by one or more methods selected from the group consisting of virus transduction, microinjection, particle bombardment, gene gun transformation and electroporation.

8. The pharmaceutical composition of claim 6, wherein the transgenic killer cell is a T cell, NK cell or CAR-T cell, and the transposon is piggybac.

9. A method of inhibiting tumor cell growth or for treating tumors, comprising administering to a subject in need thereof the transgenic killer cell of claim 1 or a pharmaceutical composition comprising the transgenic killer cell of claim 1 and pharmaceutically acceptable excipient(s).

10. The method according to claim 9, wherein the tumor is selected from the group consisting of liver cancer, lung cancer, colon cancer, pancreatic cancer, gastric cancer, breast cancer, nasopharyngeal carcinoma, lymphoma, ovarian cancer, bladder cancer, prostate cancer and head and neck tumors.

11. A pharmaceutical composition comprising the transgenic killer cell of claim 5 and a pharmaceutically acceptable excipient.

12. The pharmaceutical composition of claim 11, wherein the transgenic killer cell is a T cell, NK cell or CAR-T cell, and the transposon is piggybac.

13. A method of inhibiting tumor cell growth or for treating tumors, comprising administering to a subject in need thereof the transgenic killer cell of claim 5 or a pharmaceutical composition comprising the transgenic killer cell of claim 5 and pharmaceutically acceptable excipient(s).

14. The method according to claim 13, wherein the tumor is selected from the group consisting of liver cancer, lung cancer, colon cancer, pancreatic cancer, gastric cancer, breast cancer, nasopharyngeal carcinoma, lymphoma, ovarian cancer, bladder cancer, prostate cancer and head and neck tumors.

* * * * *